USOO5750648A

United States Patent [19]
Chang et al.

[11] Patent Number: 5,750,648
[45] Date of Patent: May 12, 1998

[54] RETROVIRAL PROTEASE INHIBITORS AND COMBINATIONS THEREOF

[75] Inventors: Min S. Chang, Glenview, Ill.; Daniel P. Getman, Chesterfield, Mo.; Richard A. Mueller, Glencoe, Ill.; James C. Ottinger, Lindenhurst, Ill.; James C. Stolzenbach, Buffalo Grove, Ill.; John J. Talley, Brentwood, Mo.; Michael L. Vazquez, Gurnee, Ill.; Gary A. Decrescenzo, St. Peters, Mo.

[73] Assignee: G.D. Searle & Co., Skokie, Ill.

[21] Appl. No.: 253,531

[22] Filed: Jun. 3, 1994

Related U.S. Application Data

[63] Continuation-in-part of Ser. No. 109,787, Aug. 20, 1993, abandoned.

[51] Int. Cl.$^6$ ........................................................ A61K 38/06
[52] U.S. Cl. .................................. 530/331; 514/18; 514/19
[58] Field of Search ........................ 514/17, 18; 530/330–332

[56] References Cited

U.S. PATENT DOCUMENTS

| H725 | 1/1990 | Gordon | 548/533 |
|---|---|---|---|
| 4,477,441 | 10/1984 | Boger et al. | 424/177 |
| 4,514,391 | 4/1985 | Gordon et al. | 514/2 |
| 4,548,926 | 10/1985 | Matsueda et al. | 514/19 |
| 4,599,198 | 7/1986 | Hoover | 260/998.2 |
| 4,616,088 | 10/1986 | Ryono et al. | 546/336 |
| 4,668,769 | 5/1987 | Hoover | 530/331 |
| 4,668,770 | 5/1987 | Boger et al. | 530/331 |
| 4,757,050 | 7/1988 | Natarajan et al. | 514/18 |
| 4,857,507 | 8/1989 | Rosenberg et al. | 514/18 |
| 4,963,530 | 10/1990 | Hemmi et al. | 514/19 |
| 4,977,277 | 12/1990 | Rosenberg et al. | 549/215 |

FOREIGN PATENT DOCUMENTS

| 0104041A1 | 3/1984 | European Pat. Off. . |
|---|---|---|
| 0172347A2 | 2/1986 | European Pat. Off. . |
| 0223437A2 | 5/1987 | European Pat. Off. . |
| 0264795A2 | 4/1988 | European Pat. Off. . |
| 0337714A2 | 10/1989 | European Pat. Off. . |
| 0342541A2 | 11/1989 | European Pat. Off. . |
| 0346847A2 | 12/1989 | European Pat. Off. . |
| 0356223A2 | 2/1990 | European Pat. Off. . |
| 0389898A2 | 10/1990 | European Pat. Off. . |
| 0393445A2 | 10/1990 | European Pat. Off. . |
| 0393457A1 | 10/1990 | European Pat. Off. . |
| 0402646A1 | 12/1990 | European Pat. Off. . |
| 0114993A2 | 8/1994 | European Pat. Off. . |
| 2184730 | 7/1987 | United Kingdom . |
| 2200115 | 7/1988 | United Kingdom . |
| 2209752 | 5/1989 | United Kingdom . |
| WO84/03044 | 8/1984 | WIPO . |
| 9208701 | 5/1992 | WIPO . |
| WO92/08701 | 5/1992 | WIPO . |
| 94/05639 | 3/1994 | WIPO . |

OTHER PUBLICATIONS

Roberts et al, *Science*, 248, 358–361, (1990).
Erickson et al, *Science*, 249, (1990).
S.J. Fittkau, *J. Prakt. Chem.*, 315, 1037 (1973).
Parikh et al, *J. Am. Chem.*, 89, 5505 (1967).
Reetz et al, *Angew. Chem. Int. Ed. Eng.*, 26:11 1141–1143 (1987).
Miller et al, *Science*, 246, 1149 (1989).
J.A. Martin, *Drugs of the Future*, 16(3), 210–212 (1991).
Kagayama et al, *Antimicrobial Agents and Chemotheraphy* 37, 810–817 (1993).
Lam et al, "De Novo Design and Discovery of Potent, Nonpeptidal HIV–1 Protease Inhibitors", paper 96 at the 205th American Chemical Society National Meeting, Medicinal Chemistry Division, Denver, CO, Mar. 28–Apr. 2, 1993.
Dorsey et al, "L–735,524: The Rational Design of a Potent and Orally Bioavailable HIV Protease Inhibitor", paper 6 at the 206th American Chemical Society National Meeting, Medicinal Chemistry Division, Chicago, IL, Aug. 22–27, 1993.
Wei et al, *J. Med. Chem.*, 36, 249–255 (1993).
Hoffman et al, *J. Med. Chem.*, 35, 3784–3791 (1992).
Saari et al, *J. Med. Chem.* 35, 3792–3802 (1992).
Romero et al, *J. Med. Chem.*, 36, 1505–1508 (1993).
Hargrave, *J. Med. Chem.*, 34, 2231–2241 (1991).
Merluzzi, *Science*, 250, 1411–1413 (1990).
Williams et al, *J. Med. Chem.*, 36, 1291–1294 (1993).
Hsu et al, *Proc. Natl. Acad. Sci. USA.* 909, 6395–6399 (1993).
Tam et al, "Tat Inhibitors: A New Class of Anti–HIV Agents" paper 372, at the 204th American Chemical Society National Meeting, Organic Chemistry Division, Washington, DC, Aug. 23–28 (1992).
Meek et al, *Nature*, 343, (1990).
T.J. McQuade et al, *Science*, 247, 454–456 (1989).
Rich et al, *Peptide Inhibitors of Proteases*, 511–520.
Rosenberg et al, *J.Med.Chem.*, 30, 1224–1228, (1987).
Pearl et al, *Nature*, 328, 482 (1987).

*Primary Examiner*—David Lukton
*Attorney, Agent, or Firm*—Banner & Witcoff, Ltd.

[57] ABSTRACT

The present invention is directed to the preparation and use of retroviral protease inhibitors and combinations of retroviral protease inhibitors which are effective in preventing the replication of mammalian retroviruses, such as human immunodeficiency virus (HIV).

17 Claims, No Drawings

RETROVIRAL PROTEASE INHIBITORS AND COMBINATIONS THEREOF

This application is a continuation-in-part of co-owned and patent application Ser. No. 08/109,787, filed Aug. 20, 1993, now abandoned, which is incorporated herein by reference in its entirety.

BACKGROUND OF THE INVENTION

1. Field of the Invention

The present invention relates to selected retroviral protease inhibitors and combinations of retroviral protease inhibitors which are effective in preventing the replication of mammalian retroviruses, such as human immunodeficiency virus (HIV). More particularly, the present invention relates to novel compounds, compositions, combinations of compounds and methods for inhibiting retroviral proteases. This invention, in particular, relates to urea-containing hydroxyethylamine protease inhibitor compounds, compositions, combinations of such compounds and method for inhibiting retroviral proteases, such as HIV protease, and for treatment or prophylaxis of retroviral infections, such as HIV infections. The subject invention also relates to processes for making such compounds as well as to intermediates useful in such processes.

2. Related Art

During the replication cycle of retroviruses, gag and gag-pol gene transcription products are translated as proteins. These proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease active site that processing of the gag precursor protein is prevented. Thus, attempts have been made to inhibit viral replication by inhibiting the action of retroviral proteases.

Retroviral protease inhibition typically involves a transition-state mimetic whereby the retroviral protease is exposed to a mimetic compound which binds (typically in a reversible manner) to the enzyme in competition with the gag and gag-pol proteins to thereby inhibit specific processing of structural proteins and the release of retroviral protease itself. In this manner, retroviral replication proteases can be effectively inhibited.

Several classes of mimetic compounds have been proposed, particularly for inhibition of proteases, such as for inhibition of HIV protease. Such mimetics include hydroxyethylamine isosteres, reduced amide isosteres and non-peptide isosteres. See for example, EP O 346 847; EP O 342,541; Roberts et al, "Rational Design of Peptide-Based Proteinase Inhibitors," Science, 248, 358 (1990); Erickson et al, "Design Activity, and 2.8 Å Crystal Structure of a C₂ Symmetric Inhibitor Complexed to HIV-1 Protease," Science, 249, 527 (1990); and S. Thaisrivongs, "Structure-Based Design of Non-Peptide HIV Protease Inhibitors," 35th Annual Buffalo Medicinal Chemistry Meeting, State University of New York at Buffalo, Buffalo, N.Y., May 22–25, 1994.

Several classes of mimetic compounds are known to be useful as inhibitors of the proteolytic enzyme renin. See, for example, U.S. Pat. No. 4,599,198; U.K. 2,184,730; G.B. 2,209,752; EP O 264 795; G.B. 2,200,115 and U.S. SIR H725. Of these, G.B. 2,200,115, GB 2,209,752, EP O 264,795, U.S. SIR H725 and U.S. Pat. No. 4,599,198 disclose urea-containing hydroxyethylamine renin inhibitors. However, it is known that, although renin and HIV proteases are both classified as aspartyl proteases, compounds which are effective renin inhibitors generally cannot be predicted to be effective HIV protease inhibitors.

U.S. Pat. No. 5,482,947 and PCT/US/93/04804 filed May 20, 1993 also provide disclosures related to the present invention.

BRIEF DESCRIPTION OF THE INVENTION

The present invention is directed to virus inhibiting compounds and compositions. More particularly, the present invention is directed to retroviral protease inhibiting compounds, compositions and combinations of such compounds, to a method of inhibiting retroviral proteases, to processes for preparing the compounds and to intermediates useful in such processes. The subject compounds are characterized as urea-containing hydroxyethylamine inhibitor compounds.

DETAILED DESCRIPTION OF THE INVENTION

In accordance with the present invention, there is provided a retroviral protease inhibiting compound of the Formula (I):

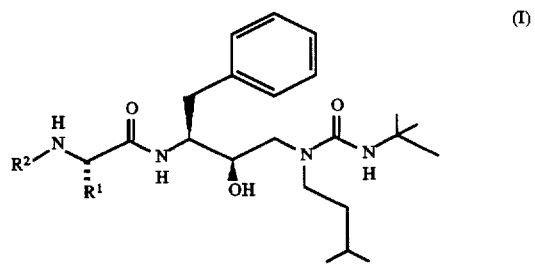

(I)

or a pharmaceutically acceptable salt or ester thereof, wherein $R^1$ is iso-propyl, sec-butyl, tert-butyl, $—C(CH_3)_2(SCH_3)$, $—C(CH_3)_2(S\{O\}CH_3)$ or $—C(CH_3)_2(S\{O\}_2CH_3)$; and $R^2$ is N-methyl-L-alaninyl, N-methyl-D-alaninyl, glycinyl, N-methylglycinyl, L-prolyl, D-prolyl or L-isoleucinyl, each of which is optionally substituted on the nitrogen atom with benzyloxycarbonyl or tert-butoxycarbonyl.

The present invention is also a method of treating a retroviral protease infection in a mammal, such as a human, monkey, cat and the like, suffering therefrom comprising administering a compound of the Formula (II):

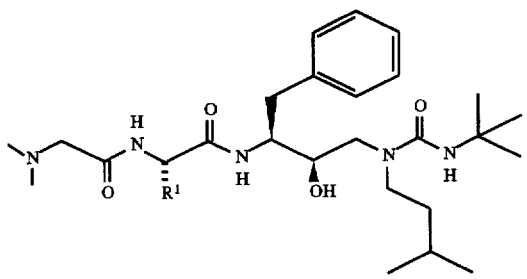

(II)

or a pharmaceutically acceptable salt thereof, wherein $R^1$ is iso-propyl, sec-butyl, tert-butyl, —$C(CH_3)_2(SCH_3)$, —$C(CH_3)_2(S\{O\}CH_3)$ or —$C(CH_3)_2(S\{O_2\}CH_3)$, in an effective amount wherein the effective amount in the mammal comprises a combination of the compound of Formula II as defined above and a compound of Formula I also as defined above, preferably for treating HIV retroviral infection. The compounds of this method preferably are of the Formula I and Formula II wherein $R^1$ is tert-butyl or sec-butyl; and $R^2$ is N-methylglycinyl.

More particularly, the present invention relates to a novel compound, butaneamide, 2-[(N-monomethylaminoacetyl) amino]-N-[3-[[[(1,1-dimethylethyl)amino]carbonyl](3-methylbutyl)amino]-2-hydroxy-1-(phenylmethyl)propyl]-3, 3-dimethyl-, [1S-[1R*(R*)),2S*]]-, selected analogs and pharmaceutically acceptable salts thereof. The novel compound may also be known as (2R,3S)-3(N-methylaminoacetyl-L-tert-butylglycinyl)amido-1-isoamyl-1-(tert-butylcarbamoyl)amino-4-phenyl-2-butanol. The structure of the novel compound is consistent with that of a metabolite obtained from its precursor or prodrug. The prodrug is butaneamide, 2-[(N,N-dimethylaminoacetyl) amino]-N-[3-[[[(1,1-dimethylethyl)amino]carbonyl](3-methylbutyl)amino]-2-hydroxy-1-(phenylmethyl)propyl]-3, 3-dimethyl-, [1S-[1R*(R*)),2S*]]-, selected analogs and pharmaceutically acceptable salt thereof, which is disclosed in co-owned U.S. Pat. No. 5,482,947 and WO Patent Application PCT/US91/08613, both incorporated herein by reference in their entirety, and is also shown in Example 1 hereinafter.

The metabolite having a formula consistent with the Formula (6)

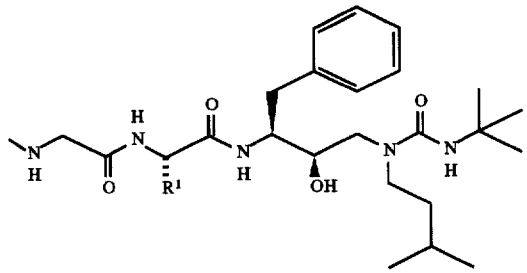

6 wherein $R^1$ is as defined above, is obtained by administering a retroviral protease inhibitor of Formula II as defined above to a mammal, collecting blood samples from the mammal, and separating the metabolite from the sample (see Example 2 infra). Thus Formula II is a precursor or prodrug. Suitable laboratory mammals from which the metabolites of the present invention can be obtained include dog, rat and the like.

Preparation of Compounds

The compounds of the Formula I of the present invention can be prepared utilizing the following general procedure.

An N-protected chloroketone derivative of an amino acid, having the Formula (1):

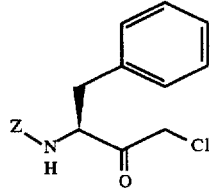

1 wherein Z represents an amino protecting group, is reduced to the corresponding alcohol utilizing an appropriate reducing agent. Suitable amino protecting groups are well known in the art and include haloacetyl or more specifically chloroacetyl, carbobenzoxy, butyryl, t-butoxycarbonyl, acetyl, benzoyl and the like. A preferred amino protecting group is carbobenzoxy or more preferably chloroacetyl. A preferred N-protected chloroketone is N-benzyloxycarbonyl-L-phenylalanine chloromethyl ketone. A preferred reducing agent is sodium borohydride. The reduction reaction is conducted at a temperature of from -10° C. to about 25° C., preferably at about 0° C., in a suitable solvent system such as, for example, tetrahydrofuran, and the like. The N-protected chloroketones are commercially available from Bachem, Inc., Torrance, Calif. Alternatively, the chloroketones can be prepared by the procedure set forth in S. J. Fittkau, J. Prakt. Chem., 315, 1037 (1973), and subsequently N-protected utilizing procedures which are well known in the art.

The resulting alcohol is then reacted, preferably at room temperature, with a suitable base in a suitable solvent system to produce an N-protected amino epoxide of the Formula (2)

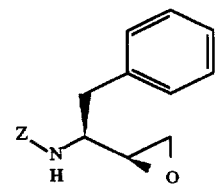

2 wherein Z is as defined above. Suitable solvent systems for preparing the amino epoxide include ethanol, methanol, isopropanol, tetrahydrofuran, dioxane, and the like including mixtures thereof. Suitable bases for producing the epoxide from the reduced chloroketone include potassium hydroxide, sodium hydroxide, potassium t-butoxide, DBU and the like. A preferred base is potassium hydroxide.

Although only one of the diastereomers is illustrated, products may be diastereomeric mixtures. The diastereomers can be separated by chromatography or, alternatively, once reacted in subsequent steps the diastereomeric products can be separated.

The amino epoxide is then reacted, in a suitable solvent system, with an equal amount, or preferably an excess of, isoamylamine. The reaction can be conducted over a wide range of temperatures, e.g., from about 10° C. to about 100° C., but is preferably, but not necessarily, conducted at a temperature at which the solvent begins to reflux. Suitable solvent systems include those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. The resulting product is the following protected amino alcohol

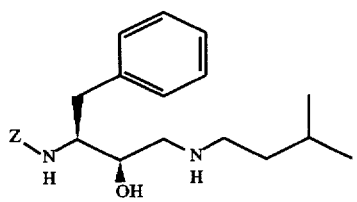

wherein Z is as defined above.

For producing compounds of Formula 3 as shown below, the resulting amino alcohol described above is then reacted, in a suitable solvent system, with a tert-butylisocyanate of the formula (tert-butyl)-NCO. Suitable solvent systems include tetrahydrofuran, methylene chloride, and the like and mixtures thereof. The resulting product is a urea derivative of the amino alcohol and can be represented by the Formula (3)

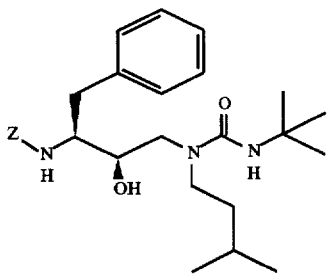

wherein Z is as defined above. The tert-butylisocyanate can be prepared by the reaction of a tert-butylamine with phosgene, triphosgene, carbodiimidazole, or carbonate $((RO)_2CO)$ under conditions well-known in the art. In addition, the tert-butylisocyanate is commercially available from Aldrich Chemical Company or may be prepared by using methods well known to those skilled in the art, e.g., an appropriate carboxylic acid and the Curtius rearrangement.

Following preparation of the urea derivative, the amino protecting group is removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative. Following neutralization of the salt, the amine is then coupled to an amino acid, for example, Z-t-butylglycine or corresponding derivative thereof represented by the formula $(ZNHCH(R^1)COOH)$, an α-amino acid, wherein Z and $R_1$ are as defined above, using standard peptide coupling methods. Such α-amino acids are well known, are commercially available or can be prepared by known methods. This produces the intermediate compounds of the present invention having the Formula (4)

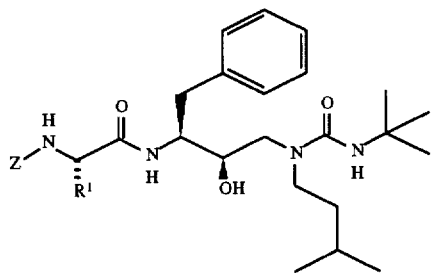

wherein Z and $R^1$ are as defined above. Preferred protecting groups in this instance are a benzyloxycarbonyl group or a t-butoxycarbonyl group. Removal of the Z protecting group from a compound of Formula 4 using conditions well known to those skilled in the art, for example, catalytic hydrogenolysis using palladium or palladium on carbon as catalysts, provides the intermediate amine. Then the intermediate amine obtained from the Formula 4 is reacted with chloroacetic anhydride to obtain the intermediate with the Formula (5)

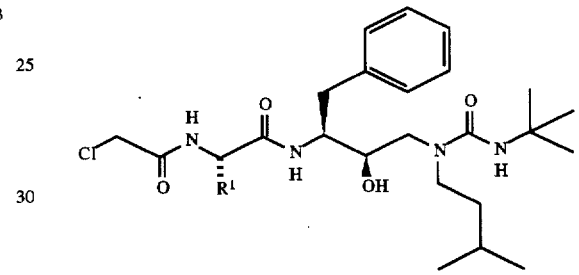

wherein $R^1$ is as defined above. Alternatively, the Z protecting group may be a chloroacetyl group which would eliminate the deprotection and acylation steps above.

The compound of Formula 6 is obtained by reacting the compound of Formula 5 with monomethylamine. Appropriate solvent systems for such a reaction include tetrahydrofuran, acetonitrile, methylene chloride, N,N-dimethylformamide, or alcohols, such as methanol, ethanol or isopropanol and the like, including mixtures thereof.

Alternatively, Formula 4 may be coupled with a Z protected N-methylglycine using standard peptide coupling methods. The compound of Formula 6 is then obtained by deprotecting the amine using the methods discussed above.

The compounds of Formula I where $R^1$ is a sulfoxide or sulfone derivative of L-penicillamine can also be prepared by oxidation of the L-penicillamine derivative of Formula I or its nitrogen protected (Z) derivative. Reagents to accomplish such oxidations are well known to those skilled in the art and include, for example, one or two equivalents of hydrogen peroxide, peracetic acid, meta-chloroperbenzoic acid, percamphoric acid, a metal salt of periodate or periodic acid or the like. Temperatures for the reaction can range from about −22° C. to about 60° C. preferably about 0° C. in the case of the sulfoxide. Solvents for the transformation include water, alcohols, dipolar aprotic solvents such as DMF, acetonitrile, nitromethane or non-protic solvents such as THF, methylene chloride, ethyl acetate and the like or mixtures of the above. Preferred conditions for preparation of the sulfoxides or their salts are sodium metaperiodate or periodic acid in water or mixtures of water with alcohols such as methanol, ethanol, denatured ethanol, isopropanol and the like carried at about 0° C.

Scheme I is illustrative of the preparation of the compounds of the present invention.

SCHEME I

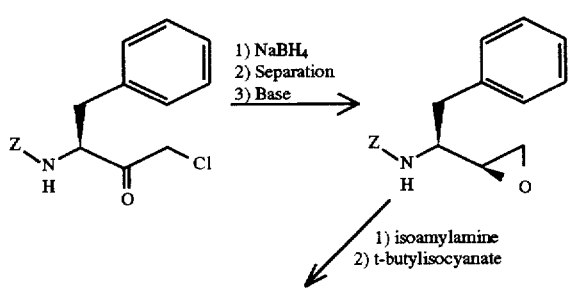
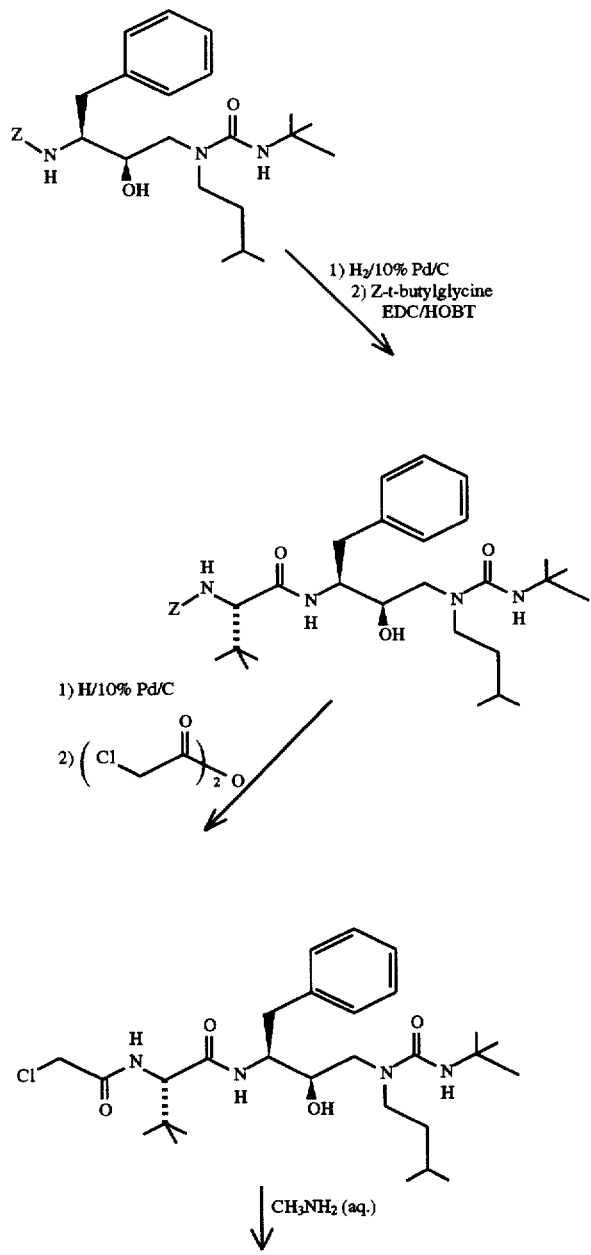
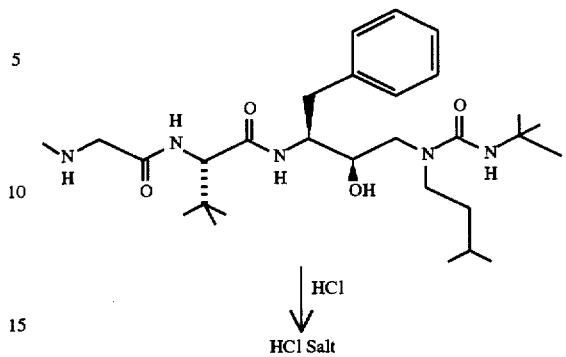

↓ HCl

HCl Salt

Alternatively, a protected amino epoxide of Formula (7) can also be used in the preparation of the compounds of the present invention:

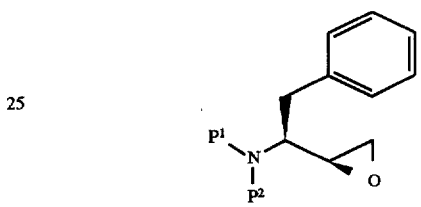

wherein $P^1$ and $P^2$ are each independently amine protecting groups, including but not limited to arylalkyl, substituted arylalkyl, cycloalkenylalkyl, substituted cycloalkenylalkyl, allyl, substituted allyl, acyl, alkoxycarbonyl, aralkoxycarbonyl or silyl. Examples of arylalkyl include, but are not limited to benzyl, ortho-methylbenzyl, trityl and benzhydryl, which can be optionally substituted with halogen, alkyl of $C_1$–$C_8$, alkoxy, hydroxy, nitro, alkylene, amino, alkylamino, acylamino and acyl, or their salts, such as phosphonium and ammonium salts. Examples of aryl groups include phenyl, naphthalenyl, indanyl, anthracenyl, durenyl, 9-(9-phenylfluorenyl) and phenanthrenyl, cycloalkenylalkyl or substituted cycloalkylenylalkyl radicals containing cycloalkyls of $C_6$–$C_{10}$. Suitable acyl groups include carbobenzoxy, t-butoxycarbonyl, iso-butoxycarbonyl, benzoyl, substituted benzoyl, butyryl, acetyl, tri-fluoroacetyl, tri-chloroacetyl, phthaloyl and the like.

The term silyl refers to a silicon atom optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis (dimethylsilyl)benzene, 1,2-bis(dimethylsilyl)ethane and diphenylmethylsilyl. Silylation of the amine functions to provide mono- or bis-disilylamine can provide derivatives of the aminoalcohol, amino acid, amino acid esters and amino acid amide. In the case of amino acids, amino acid esters and amino acid amides, reduction of the carbonyl function provides the required mono- or bis-silyl aminoalcohol. Silylation of the aminoalcohol can lead to the N,N,O-tri-silyl derivative. Removal of the silyl function from the silyl ether function is readily accomplished by treatment with, for example, a metal hydroxide or ammonium flouride reagent, either as a discrete reaction step or in situ during the preparation of the amino aldehyde reagent. Suitable silylating agents are, for example, trimethylsilyl chloride, tert-buty-dimethylsilyl chloride, phenyldimethylsilyl chlorie, diphenylmethylsilyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Additionally, $P^1$ and $P^2$ can form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, e.g., nitrophthalimidyl.

The economical and safe large scale method of preparation of protease inhibitors of the present invention can alternatively utilize amino acids or amino alcohols to form N,N-protected alpha aminoalcohol of the Formula (8)

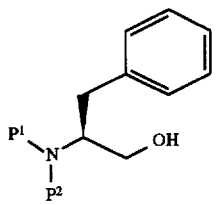

8 wherein $P^1$ and $P^2$ are described above. A general method for the preparation of amino epoxides, useful as intermediates in the synthesis of HIV protease inhibitors is shown in Scheme 2.

Preferably, the amine protecting groups $P^1$ and $P^2$ are introduced by alkylation of the amine group such as by the addition of suitable alkylating agents in an appropriate solvent in the presence of base. Preferred bases used in alkylation include sodium hydroxide, sodium bicarbonate, potassium hydroxide, lithium hydroxide, potassium carbonate, sodium carbonate, cesium hydroxide, magnesium hydroxide, calcium hydroxide or calcium oxide, or tertiary amine bases such as triethyl amine, diisopropylethylamine, N-methylpiperidine, pyridine, dimethylaminopyridine and azabicyclononane. Reactions can be homogenous or heterogenous. Suitable solvents are water and protic solvents or solvents miscible with water, such as methanol, ethanol,

SCHEME 2

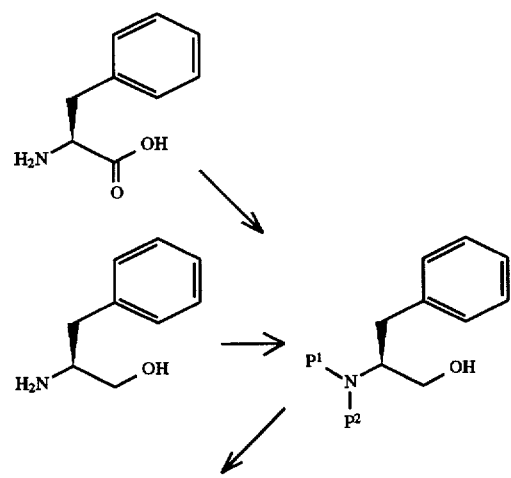

-continued
SCHEME 2

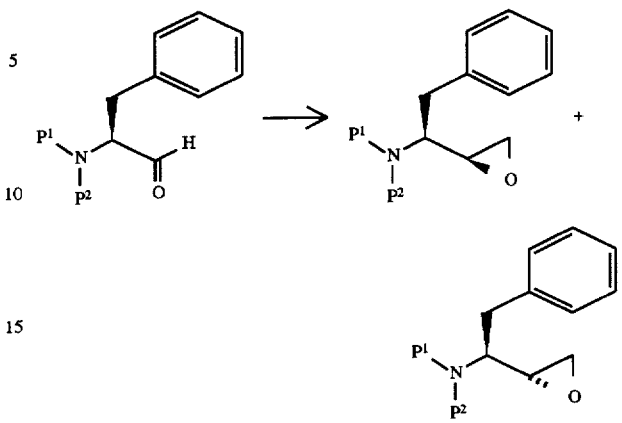

isopropyl alcohol, tetrahydrofuran and the like, with or without added water. Dipolar aprotic solvents may also be used with or without added protic solvents including water. Examples of dipolar aprotic solvents include acetonitrile, dimethylformamide, dimethyl acetamide, acetamide, tetramethyl urea and its cyclic analog, dimethylsulfoxide, N-methylpyrrolidone, sulfolane, nitromethane and the like. Reaction temperature can range between about $-20°$ to $100°$ C. with the preferred temperature of about $25°-85°$ C. The reaction may be carried out under an inert atmosphere such as nitrogen or argon, or normal or dry air, under atmospheric pressure or in a sealed reaction vessel under positive pressure. The most preferred alkylating agents are benzyl bromide or benzyl chloride or monosubstituted aralkyl halides or polysubstituted aralkyl halides. Sulfate or sulfonate esters are also suitable reagents to provide the corresponding benzyl analogs and they can be preformed from the corresponding benzyl alcohol or formed in situ by methods well known to those skilled in the art. Trityl, benzhydryl, substituted trityl and substituted benzhydryl groups, independently, are also effective amine protecting groups as are allyl and substituted allyl groups. Their halide derivatives can also be prepared from the corresponding alcohols by methods well known to those skilled in the art such as treatment with thionyl chloride or bromide or with phosphorus tri- or pentachloride, bromide or iodide or the corresponding phosphoryl trihalide. Examples of groups that can be substituted on the aryl ring include alkyl, alkoxy, hydroxy, nitro, halo and alkylene, amino, mono- and dialkyl amino and acyl amino, acyl and water solubilizing groups such as phosphonium salts and ammonium salts. The aryl ring can be derived from, for example, benzene, napthelene, indane, anthracene, 9-(9-phenyl fluorenyl, durene, phenanthrene and the like. In addition, 1,2-bis (substituted alkylene) aryl halides or sulfonate esters can be used to form a nitrogen containing aryl or non-aromatic heterocyclic derivative [with $P^1$ and $P^2$] or bis-heterocycles. Cycloalkylenealkyl or substituted cyloalkylene radicals containing 6–10 carbon atoms and alkylene radicals constitute additional acceptable class of substituents on nitrogen prepared as outlined above including, for example, cyclohexylenemethylene.

Compounds of Formula 8 can also be prepared by reductive alkylation by, for example, compounds and intermediates formed from the addition of an aldehyde with the amine and a reducing agent, reduction of a Schiff Base, carbinolamine or enamine or reduction of an acylated amine derivative. Reducing agents include metals, such as platinum, palladium, palladium hydroxide, palladium on carbon, platinum oxide, rhodium and the like, in the presence of hydrogen gas or hydrogen transfer molecules such as cyclohexene, cyclohexadiene and the like, or hydride agents such as lithium aluminumhydride, sodium borohydride, lithium borohydride, sodium cyanoborohydride, diisobutylaluminum hydride, lithium tri-tert-butoxyaluminum hydride and the like.

Additives such as sodium or potassium bromide, sodium or potassium iodide can catalyze or accelerate the rate of amine alkylation, especially when benzyl chloride was used as the nitrogen alkylating agent.

Phase transfer catalysis wherein the amine to be protected and the nitrogen alkylating agent are reacted with base in a solvent mixture in the presence of a phase transfer reagent, catalyst or promoter. The mixture can consist of, for example, toluene, benzene, ethylene dichloride, cyclohexane, methylene chloride or the like with water or a aqueous solution of an organic water miscible solvent such as THF. Examples of phase transfer catalysts or reagents include tetrabutylammonium chloride or iodide or bromide, tetrabutylammonium hydroxide, tri-butyloctylammonium chloride, dodecyltrihexylammonium hydroxide, methyltrihexylammonium chloride and the like.

A preferred method of forming substituted amines involves the aqueous addition of about 3 moles of organic halide to the amino acid or about 2 moles to the aminoalcohol. In a more preferred method of forming a protected amino alcohol, about 2 moles of benzylhalide in a basic aqueous solution is utilized. In an even more preferred method, the alkylation occurs at 50° C. to 80° C. with potassium carbonate in water, ethanol/water or denatured ethanol/water. In a more preferred method of forming a protected amino acid ester, about 3 moles of benzylhalide is added to a solution containing the amino acid.

The protected amino acid ester is reduced to the protected amino alcohol in an organic solvent. Preferred reducing agents include lithium aluminiumhydride, lithium borohydride, sodium borohydride, borane, lithium tri-ter-butoxyaluminum hydride, borane•THF complex and the like. Most preferably, the reducing agent is diisobutylaluminum hydride (DiBAL-H) in toluene. These reduction conditions provide an alternative to a lithium aluminum hydride reduction.

The protected alpha amino alcohol is oxidized to form a chiral amino aldehyde of the Formula (9)

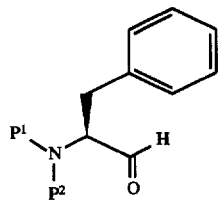

9 wherein $P^1$ and $P^2$ are as defined above. Acceptable oxidizing reagents include, for example, sulfur trioxide-pyridine complex and DMSO, oxalyl chloride and DMSO, acetyl chloride or anhydride and DMSO, trifluoroacetyl chloride or anhydride and DMSO, methanesulfonyl chloride and DMSO or tetrahydrothiaphene-S-oxide, toluenesulfonyl bromide and DMSO, trifluoromethanesulfonyl anhydride (triflic anhydride) and DMSO, phosphorus pentachloride and DMSO, dimethylphosphoryl chloride and DMSO, isobutylchloroformate and DMSO, and the like (Reetz et al., Angew Chem., 99, p. 1186, (1987); Angew Chem. Int. Ed. Engl., 26, p. 1141, (1987); employed oxalyl chloride and DMSO at −78° C.).

A preferred oxidation method is sulfur trioxide pyridine complex, triethylamine and DMSO at room temperature. This system provides excellent yields of the desired chiral protected amino aldehyde usable without the need for purification by chromatography and large scale operations are made less hazardous. Reaction at room temperature also eliminates the need for the use of low temperature conditions.

The reaction may be carried out under and inert atmosphere such as nitrogen or argon, or normal or dry air, under atmospheric pressure or in a sealed reaction vessel under positive pressure. Preferred is a nitrogen atmosphere. Alternative amine bases include, for example, tri-butyl amine, tri-isopropyl amine, N-methylpiperidine, N-methyl morpholine, azabicyclononane, diisopropylethylamine, 2,2, 6,6-tetramethylpiperidine, N,N-dimethylaminopyridine, or mixtures of these bases. Triethylamine is a preferred base. Alternatives to pure DMSO as solvent include mixtures of DMSO with non-protic or halogenated solvents such as tetrahydrofuran, ethyl acetate, toluene, xylene, dichloromethane, ethylene dichloride and the like. Dipolar aprotic co-solvents include acetonitrile, dimethylformamide, dimethylacetamide, acetamide, tetramethyl urea and its cyclic analog, N-methylpyrrolidone, sulfolane and the like. Rather than N,N-dibenzylphenylalaninol as the aldehyde precursor, the phenylalaninol derivatives discussed above can be used to provide the corresponding N-monosubstituted or N,N-disubstituted aldehyde.

In addition, hydride reduction of an amide or ester derivative of the corresponding alkyl, benzyl or cycloalkenyl nitrogen protected phenylalanine, substituted phenylalanine or cycloalkyl analog of phenylalanine derivative can be carried out to provide a compound of Formula 8. Hydride transfer is an additional method of aldehyde synthesis under conditions where aldehyde condensations are avoided, cf, Oppenauer Oxidation.

The aldehydes of this process can also be prepared by methods of reducing protected phenylalanine and phenylalanine analogs or their amide or ester derivatives by, e.g., sodium amalgam with HCl in ethanol or lithium or sodium or potassium or calcium in ammonia. The reaction temperature may be from about −35° C. to about 45° C., and preferably from about 5° C. to about 25° C. or when the concentration of ammonia approaches 100% the temperature is preferably about −33° C. Two additional methods of obtaining the nitrogen protected aldehyde include oxidation of the corresponding alcohol with bleach in the presence of a catalytic amount of 2,2,6,6-tetramethyl-1-pyridyloxy free radical. In a second method, oxidation of the alcohol to the aldehyde is accomplished by a catalytic amount of tetrapropylammonium perruthenate in the presence of N-methylmorpholine-N-oxide.

Alternatively, an acid chloride derivative of a protected phenylalanine or phenylalanine derivative as disclosed above can be reduced with hydrogen and a catalyst such as Pd on barium carbonate or barium sulphate, with or without an additional catalyst moderating agent such as sulfur or a thiol (Rosenmund Reduction).

An important aspect for this preparation of an appropriate amino-epoxide useful as an intermediate to prepare a compound of the present invention is a reaction involving the addition of chloromethyllithium or bromomethyllithium to the α-amino aldehyde, e.g. addition of chloromethyllithium or bromomethyllithium to racemic or chiral amino aldehydes to form aminoepoxides of the Formula 10

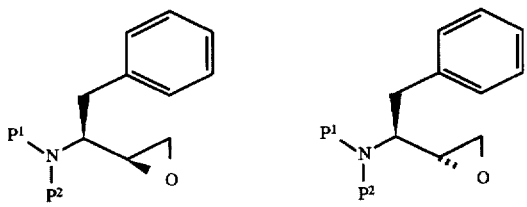

wherein P¹ and P² are as defined above. The addition of chloromethyllithium or bromomethyllithium to a chiral amino aldehyde is highly diastereoselective. Preferably, the chloromethyllithium or bromomethyllithium is generated in-situ from the reaction of the dihalomethane and n-butyllithium. Acceptable methyleneating halomethanes include chloroiodomethane, bromochloromethane, dibromomethane, diiodomethane, bromofluoromethane and the like. The sulfonate ester of the addition product of, for example, hydrogen bromide to formaldehyde is also a methyleneating agent. Tetrahydrofuran is the preferred solvent, however alternative solvents such as toluene, dimethoxyethane, ethylene dichloride, methylene chloride can be used as pure solvents or as a mixture. Dipolar aprotic solvents such as acetonitrile, DMF, N-methylpyrrolidone are useful as solvents or as part of a solvent mixture. The reaction can be carried out under an inert atmosphere such as nitrogen or argon. For n-butyl lithium can be substituted other organometallic reagents such as methyllithium, tert-butyl lithium, sec-butyl lithium, phenyllithium, phenyl sodium and the like. The reaction can be carried out at temperatures of between about −80° C. to 0° C. but preferably between about −80° C. to −20 C. The most preferred reaction temperatures are between −40° C. to −15° C. Reagents can be added singly but multiple additions are preferred in certain conditions. The preferred pressure of the reaction is atmospheric however a positive pressure is valuable under certain conditions such as a high humidity environment.

Alternative methods of conversion to the epoxides of this invention include substitution of other charged methylenation precursor species followed by their treatment with base to form the analogous anion. Examples of these species include trimethylsulfoxonium tosylate or triflate, tetramethylammonium halide, methyldiphenylsulfoxonium halide wherein halide is chloride, bromide or iodide.

The conversion of the aldehydes of this invention into their epoxide derivative can also be carried out in multiple steps. For example, the addition of the anion of thioanisole prepared from, for example, a butyl or aryl lithium reagent, to the protected aminoaldehyde, oxidation of the resulting protected aminosulfide alcohol with well known oxidizing agents such as hydrogen peroxide, tert-butyl hypochlorite, bleach or sodium periodate to give a sulfoxide. Alkylation of the sulfoxide with, for example, methyl iodide or bromide, methyl tosylate, methyl mesylate, methyl triflate, ethyl bromide, isopropyl bromide, benzyl chloride or the like, in the presence of an organic or inorganic base Alternatively, the protected aminosulfide alcohol can be alkylated with, for example, the alkylating agents above, to provide a sulfonium salts that are subsequently converted into the subject epoxides with tert-amine or mineral bases.

The desired epoxides form, using most preferred conditions, diastereoselectively in ratio amounts of at least about an 85:15 ratio (S,S:S,R). The product can be purified by chromatography to give the diastereomerically and enantiomerically pure product but it is more conveniently used directly without purification to prepare the HIV protease inhibitors of the present invention.

The diastereomers can be separated by chromatography or, alternatively, once reacted in subsequent steps the diastereomeric products can be separated.

As described above, the amino epoxide is then reacted, in a suitable solvent system, with at least an equal amount, preferably an excess, of isoamylamine. The reaction can be conducted over a wide range of temperatures, e.g., from about 10° C. to about 100° C. but is preferably, but not necessarily, conducted at a temperature at which the solvent begins to reflux. Suitable solvent systems include those wherein the solvent is an alcohol, such as methanol, ethanol, isopropanol, and the like, ethers such as tetrahydrofuran, dioxane and the like, and toluene, N,N-dimethylformamide, dimethyl sulfoxide, and mixtures thereof. A preferred solvent is isopropanol. The resulting product is a protected amino alcohol.

This protected amino alcohol can then be reacted, with tertiary-butylisocyanate and the protecting groups, P¹ and P², removed using methods well known to those skilled in the art. For example, when P¹ and P² are both benzyl groups, these can be removed by hydrogenolysis using a palladium catalyst. The resulting amine can then be converted into the desired product through the methods outlined in Scheme 1 above or in an analogous manner for the anaolgous and pharmaceutically acceptable salts of the invention.

The chemical reactions described above are generally disclosed in terms of their broadest application to the preparation of the compounds of this invention. The reactions can be successfully performed using conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on either a Varian VXR-300 or VXR-400 nuclear magnetic resonance spectrometer.

Example 1

Butaneamide, 2-[(N,N-dimethylaminoacetyl)amino]-N-[3-[[[(1,1-dimethylethyl)amino]carbonyl](3-methylbutyl)amino]-2-hydroxy-1-(phenylmethyl)propyl]-3,3-dimethyl-, [1S-[1R*(R*), 2S*]]-

To a solution of N,N-dimethylaminoacetic acid (62 mg, 0.6 mmol) and N-hydroxybenzotriazole (87 mg, 0.57 mmol) in 2 mL of DMF at 0° C. was added EDC (109 mg, 0.57 mmol). The reaction mixture was stirred for 1 hour and then (2R, 3S)-3-(L-tert-butylglycinyl) amido-1-isoamyl 1(tert-butylcarbamoyl) amino-4-phenyl-2-butanol (231 mg, 0.5 mmol) as prepared in WO/US91/08613, Example 23, Part C, was added. The reaction was stirred at room temperature for 16 hours and then concentrated in vacuo. The residue was chromatographed on silica (50 gm) using 5% ethanol in dichloromethane. The butaneamide, 2-[(2,2-dimethylaminoacetyl) amino]-N-[3-[[[(1,1-dimethylethyl)amino]carbonyl](3-methylbutyl)amino]-2-hydroxy-1-(phenylmethyl)propyl]-3,3-dimethyl-, [1S-[1R*(R*)),2S*]]- was obtained as a white solid. Anal. Calc'd for $C_{30}H_{53}N_5O_4 \cdot 0.3 H_2O$: C, 65.13; H, 9.77; N, 12.66. Found: C, 65.10; H, 9.79; N, 12.52.

Example 2

Step A: N-Cbz-3-(S)-amino-1-chloro-4-phenyl-2(S)-butanol

To a solution of 20 gm (60 mmol) of N-benzyloxycarbonyl-L-phenylalanine chloromethyl ketone in MeOH (215 mL) and THF (215 mL) at 0° C., was added portionwise, 3.52 gm (92 mmol) of solid sodium borohydride. After 15 minutes the reaction mixture was concentrated to a solid and dissolved in ethyl acetate (200 mL). The ethyl acetate solution was washed with 1M aqueous, noncompetitive, and saturated aqueous NaCl (150 mL each). The organic layer was dried over $Na_2SO_4$, filtered and concentrated to give a white solid. The solid was triturated with hot hexane and filtered. The resulting solid was recrystallized from ethyl acetate and hexane to give 7.43 gm of a white solid (37%). The mother liquor was concentrated and the residue recrystallized to afford a second crop of the desired product, N-Cbz-3-(S)-amino-1-chloro-4-phenyl-2 (S)-butanol, 2.1 gm (18%), mp 150°–151° C.

Step B: N-Cbz-3-(S)-amino-1,2-(S)-epoxy-4-phenylbutane

N-Cbz-3-(S)-amino-1-chloro-4-phenyl-2(S)-butanol (9.5 gm, 28 mmol) was added to a solution of KOH (1.9 gm, 34 mmol) in absolute ethanol (250 mL). After 15 minutes the solvent was removed and the residue dissolved in $CH_2Cl_2$ (100 mL). The organic solution was washed with water (100 mL) and dried ($MgSO_4$). Filtration and concentration afforded a white solid, 7.4 gm (87%). Anal. Calc'd for $C_{18}H_{19}NO_3$: C, 72.71; H, 6.44; N, 4.71. Found: C, 72.16; H, 6.42; N, 4.65.

Step C: N-[[3(S)-phenylmethylcarbamoyl)amino-2(R)-hydroxy-4-phenylbutyl]-N-[(3-methylbutyl)]amine N-Cbz-3-(S)-amino-1,2-(S)-epoxy-4-phenylbutane (10 gm, 33.6 mmol) and isoamylamine (19.5 mL, 168 mmol) were combined in isopropanol (100 mL) and stirred for 16 hours at room temperature. The insoluble material was collected by filtration, washed with a small amount of isopropanol and then n-hexane. The material was then dried in vacuo to afford a white solid N-[[3(S)-phenylmethylcarbamoyl)amino-2(R)-hydroxy-4-phenylbutyl]N-[(3-methylbutyl)]amine, 10.5 gm (81%).

Step D: (2R, 3S)-3-(phenylmethoxycarbonyl)amino-2-hydroxy-4-phenyl-1-[N-(3-methylbutyl)-N-[(1,1-dimethylethyl)amino]carbonyl]aminobutane To a solution of N-[[3(S)-phenylmethylcarbamoyl)amino-2(R)-hydroxy-4-phenylbutyl]-N-[(3-methylbutyl)]amine (10.5 gm, 27 mmol) in $CH_2Cl_2$ (85 mL) was added t-butylisocyanate (3.1 mL, 27 mmol). After 5 minutes the reaction mixture was concentrated, the residue taken up in ethyl acetate (100 mL), and washed with 5% aqueous citric acid and saturated aqueous NaCl (50 mL each). The organic solution was dried ($Na_2SO_4$), filtered and concentrated to a foamy white solid, 11.84 gm. This was chromatographed on silica using 1:1 ethyl acetate/hexane as the eluting solvent to afford a white solid, 10.7 gm (72%). m/z=597

Step E: (2R, 3S)-3-amino-2-hydroxy-4-phenyl-1-[N-(3-methylbutyl)-N-[(1,1-dimethylethyl)amino]carbonyl] aminobutane A solution of (2R, 3S)-3-(phenylmethoxycarbonyl) amino-2-hydroxy-4-phenyl-1-[N-(3-methylbutyl)-N-[(1,1-dimethylethyl)amino]carbonyl]aminobutane (10.7 gm, 22.1 mmol) in methanol (50 mL) was hydrogenated over 10% palladium-on-carbon for 1 hour, filtered through diatomaceous earth and concentrated to an oil, 7.3 gm (95%).

Step F: (2R, 3S)-3-(N-benzyloxycarbonyl-L-tert-butylglycinyl) amino-2-hydroxy-4-phenyl-1-[N-(3-methylbutyl)-N-[(1,1-dimethylethyl)amino]carbonyl] aminobutane A solution of N-Cbz-tert-butylglycine (5.35 gm, 20.2 mmol) and N-hydroxybenzotriazole (2.60 mg, 19.3 mmol) in 30 mL of dimethylformamide was combined with EDC (3.70 mg, 19.3 mmol). The reaction was stirred for 1 hour and then (2R, 3S)-3-amino-2-hydroxy-4-phenyl-1-[N-(3-methylbutyl)-N-[(1,1-dimethylethyl)amino]carbonyl] aminobutane (6.3 mg, 18.0 mmol) in 30 mL of DMF was added. The reaction was stirred at room temperature for 16 hours then concentrated. The residue was taken up in ethyl acetate (50 mL) and extracted with 0.5N HCl, saturated NaHCO3 solution, and saturated NaCl (25 mL) each. The solution was dried over $Na_2SO_4$, filtered and concentrated to a white foam, yield 9.21 gm (86%). m/z=597.

Step G: (2R, 3S)-3-(L-tert-butylglycinyl)amino-2-hydroxy-4-phenyl-1-[N-(3-methylbutyl)-N-[(1,1-dimethylethyl) amino]carbonyl]aminobutane A solution of (2R, 3S)-3-(N-benzyloxycarbonyl-L-tert-butylglycinyl) amino-2-hydroxy-4-phenyl-1-[N-(3-methylbutyl)-N-[(1,1-dimethylethyl)amino]carbonyl] aminobutane (9.21 gm, 15.4 mmol) in 50 mL of methanol was hydrogenated over 10% palladium-on-carbon for 0.75 hours to give the product as a white foam, yield 6.9 gm (96%).

Step H: (2R, 3S)-3-(N-chloroacetyl-L-tert-butylglycinyl) amino-2-hydroxy-4-phenyl-1-[N-(3-methylbutyl)-N-[(1,1-dimethylethyl)amino]carbonyl]aminobutane To a solution of (2R, 3S)-3-(L-tert-butylglycinyl)amino-2-hydroxy-4-phenyl-1-[N-(3-methylbutyl)-N-[(1,1-dimethylethyl)amino]carbonyl]aminobutane (6.89 gm, 14.9 mmol) and N,N-diisopropylethylamine (3.1 mL, 17.8 mmol) in 120 mL of dichloromethane was added chloroacetic anhydride (2.8 gm, 16.4 mmol). After 90 minutes at room temperature the solvent was removed on a rotary evaporator and the residue taken up in ethyl acetate (50 mL) and washed with 5% aqueous citric acid, saturated aqueous NaHCO3 and saturated aqueous NaCl (25 mL) each. The product precipitated from the ethyl acetate solution and was collected by suction filtration. Obtained as a white solid, yield 6.9 gm (85%). Anal. Calc'd for $C_{28}H_{47}N_4O_4Cl \cdot 0.5 H_2O$: C, 61.35; H, 8.83; N, 10.22. Found: C, 61.55; H, 8.81; N, 10.04.

Step I: (2R, 3S)-3(N-methylaminoacetyl-L-tert-butylglycinyl) amino-2-hydroxy-4-phenyl-1-[N-(3-methylbutyl)-N-[(1,1-dimethylethyl)amino]carbonyl] aminobutane or butaneamide, 2-[(N-monomethylaminoacetyl)amino]-N-[3-[[[(1,1-dimethylethyl)amino]carbonyl](3-methylbutyl)amino]-2-hydroxy-1-(phenylmethyl)propyl]-3,3-dimethyl-, [1S-[1R*(R*)),2S*]]-

To a solution of (2R, 3S)-3-(N-chloroacetyl-L-tert-butylglycinyl)amino-2-hydroxy-4-phenyl-1-[N-(3-methylbutyl)-N-[(1,1-dimethylethyl)amino]carbonyl] aminobutane (3.8 gm, 7.1 mmol) in ethanol (21 mL) was added 40% aqueous methylamine (21 mL). The reaction was stirred at room temperature for one hour then concentrated on a rotary evaporator. The residue was dissolved in ethyl acetate (50 mL) and washed 75% saturated NaCl solution, dried over MgSO4 and concentrated to a white solid, yield 3.5 gm (92%). DSC 160.28'C.

Step J: (2R, 3S)-3(N-methylaminoacetyl-L-tert-butylglycinyl)amino-2-hydroxy-4-phenyl-1-[N-(3-methylbutyl)-N-[(1 1-dimethylethyl)amino]carbonyl] aminobutane hydrochloride or butaneamide, 2-[(N-monomethylaminoacetyl)amino]-N-[3-[[[(1,1-dimethylethyl)amino]carbonyl](3-methylbutyl)amino]-2-hydroxy-1-(phenylmethyl)propyl]-3,3-dimethyl-, [1S-[1R*(R*)), 2S*]]-, hydrochloride To a solution of (2R, 3S)-3(N-methylaminoacetyl-L-tert-butylglycinyl) amino-2-hydroxy-4-phenyl-1-[N-(3- methylbutyl)-N-[(1,1-dimethylethyl)amino]carbonyl] aminobutane or butaneamide, 2-[(N-monomethylaminoacetyl) amino]-N-[3-[[[(1,1-dimethylethyl)amino]carbonyl](3-methylbutyl)amino]-2-hydroxy-1-(phenylmethyl)propyl]-3,3-dimethyl-, [1S-[1R*(R*)),2S*]]- (1.46 gm, 2.7 mmol) in methanol (15 mL) was added concentrated HCl (250 uL) in methanol (10 mL). The solvent was removed on a rotary evaporator and the resulting solid recrystallized from ethyl acetate (20 mL). The white solid was collected by suction filtration and washed with diethyl ether, then dried in-vacuo, yield 1.4 gm (91%). Anal. Calc'd for $C_{29}H_{52}N_5O_4Cl$: C, 61.08; H, 9.19; N, 12.28; Cl, 6.22. Found: C, 61.01; H, 9.56; N, 12.27; Cl, 6.41. DSC 187.02'C.

Example 3
(2R,3S)-3-(N,N-dimethylaminoacetyl-L-isoleucinyl)amido-1-[N-isoamyl-N-(tert-butylcarbamoyl)]amino-4-phenyl-2-butanol or butaneamide, 2-[(N,N-dimethylaminoacetyl)amino]-N-[3-[[[(1,1-dimethylethyl)amino]carbonyl](3-methylpentyl)amino]-2-hydroxy-1-(phenylmethyl)propyl]-3,3-dimethyl-, [1S-[1R*(R*)), 2S*]]-

To a solution of (2R,3S)-3-N-chloroacetyl-L-isoleucine)amido-1-[N-isoamyl-N-(tert-butylcarbamoyl)]amino-4-phenyl-2-butanol, (1.61 g, 2.98 mmol) in 30 mL of dioxane is added 3.0 mL of 50 wt % aqueous dimethylamine and stirred in a closed vessel for 15 hrs. The solution is concentrated and diluted with 100 mL of ethyl acetate and washed with saturated sodium bicarbonate, and brine. The organic layer is dried over magnesium sulfate, filtered, and concentrated to yield 1.50 grams of crude material, which is chromatographed over silica gel using a 4% methanol dichloromethane eluant to yield 1.03 grams of purified product, (2R,3S)-3-(N,N'-dimethylaminoacetyl-L-isoleucine)amido-1-[N-isoamyl-N-(tert-butylcarbamoyl)]amino-4-phenyl-2-butanol or butaneamide, 2-[(N,N-dimethylaminoacetyl)amino]-N-[3-[[[(1,1-dimethylethyl)amino]carbonyl](3-methylpentyl)amino]-2-hydroxy-1-(phenylmethyl)propyl]-3,3-dimethyl-, [1S-[1R*(R*)),2S*]] -, M+H=548 mp 72°-3° C.

Example 4
Step A: (2R,3S)-3(N-tert-butyloxycarbonyl-L-isoleucinyl)amido-1-[N-isoamyl-N-(tert-butylcarbamoyl)]amino-4-phenyl-2-butanol A solution of (2R,3S)-3-amino-1-[N-isoamyl-N-(tert-butylcarbamoyl)]amino-4-phenyl-2-butanol(2.44 g, 6.8 mmol) in 20 mL of dichloromethane and N-Boc-isoleucine-N-hydroxysuccinamide ester (2.26 g, 6.8 mmol) is stirred for 16 h. The solution is extracted with 50 mL of saturated sodium bicarbonate 50 mL of 5% aqueous citric acid, and dried over magnesium sulfate, filtered, and concentrated on a rotary evaporator to yield 3.58 g of product which is recrystallized from ethyl acetate/hexanes. M+H=563.
Step B: (2R,3S)-3-(L-isoleucinyl)amido-1-[N-isoamyl-N-(tert-butylcarbamoyl)]amino-4-phenyl-2-butanol hydrochloride salt A solution of (2R,3S)-3-(N-tert-butyloxycarbonyl-L-isoleucinyl)amido-1-[N-isoamyl-N-(tert-butylcarbamoyl)amino-4-phenyl-2-butanol (3.58 g, 6.7 mmol) is dissolved in 40 mL of 4N HCl in dioxane and stirred for 1.5 h. The solution is concentrated on a rotary evaporator and chased three times with diethyl ether to yield 2.51 g of hydrochloride salt.
Step C: (2R,3S)-3-(N-chloroacetyl-L-isoleucinyl)amido-1-[N-isoamyl-N-(tert-butylcarbamoyl)]amino-4-phenyl-2-butanol To a solution of (2R,3S)-3-(L-isoleucinyl)amido-1-[N-isoamyl-N-(tert-butylcarbamoyl)]amino-4-phenyl-2-butanol, hydrochloride salt, (2.51 g, 5.02 mmol) in tetrahydrofuran is added 1.0 g of N-methylmorpholine followed by (860 mg, 5.0 mmol) of chloroacetic anhydride and stirred for three hours. The contents are concentrated on a rotary evaporator and diluted with 150 mL of ethyl acetate, washed with 5% aqueous potassium hydrogen sulfate, and 50 mL of saturated sodium chloride. The organic phase is dried over magnesium sulfate, filtered and concentrated to yield 1.9 g of crude material which is chromatographed over silica gel using an ethyl acetate hexanes eluant to yield 1.6 g of crystalline material, mp 165°-6° C. M+H=540.
Step D: (2R,3S)-3-(N-methylaminoacetyl-L-isoleucinyl)amido-1-[N-isoamyl-N-(tert-butylcarbamoyl)]amino-4-phenyl-2-butanol or butaneamide, 2-[(N-monomethylaminoacetyl)amino]-N-[3-[[[(1,1-dimethylethyl)amino]carbonyl](3-methylpentyl)amino]-2-hydroxy-1-(phenylmethyl)propyl]-3,3-dimethyl-, [1S-[1R*(R*)),2S*]]-

To a solution of (2R,3S)-3-(N-chloroacetyl-L-isoleucinyl) amido-1-[N-isoamyl-N-(tert-butylcarbamoyl)]amino-4-phenyl-2-butanol, 300 mg in 5 mg in 5 mL of tetrahydrofuran is added 1.5 mL of 40% aqueous methylamine and stirred for 4 hours and concentrated on a rotary evaporator. The residue is dissolved in 50 mL of ethyl acetate and washed with water. The organic phase is dried over magnesium sulfate, filtered and concentrated to yield 249 mg of crude material which is recrystallized from ethyl acetate isooctane to yield 149 mg of desired product. HRMS calculated 534.4019, found 534.3956. mp=133°-134° C.

Example 5
PART I
Step A: (2R, 3S)-3-(N-tert-butyloxycarbonyl-S-methyl-L-penicillaminyl)amido-1-[N-isoamyl-N-(tert-butylcarbamoyl)]amino-4-phenyl-2-butanol To a solution of N-Boc-S-methyl-L-penicillamine (513 mg, 1.9 mmol) and N-hydroxybenzotriazole (298 mg, 1.9 mmol) in 2 mL of dimethylformamide, cooled to 0° C., was added EDC (345 mg, 1.8 mmol). The reaction was stirred for 30 minutes and then (2R, 3S)-3-amino-1-[N-isoamyl-N-(tert-butylcarbamoyl)]amino-4-phenyl-2-butanol hydrochloride (577 mg, 1.5 mmol) in 2 mL of DMF and N-methylmorpholine (181 uL, 1.6 mmol) was added. The reaction was stirred at room temperature for 16 hours then poured into 50% saturated aqueous $NaHCO_3$ solution. The solid was collected by suction filtration washed with water and dried in-vacuo. The solid was chromatographed on silica gel (50 gm) using 2% methanol in dichloromethane as the eluting solvent. The product was obtained as a white solid, 416 mg (47%). m/z=595.
Step B: (2R, 3S)-3-(S-methyl-L-penicillaminyl)amido-1-[N-isoamyl-N-(tert-butylcarbamoyl)]amino-4-phenyl-2-butanol hydrochloride To a solution of (2R, 3S)-3-(N-tert-butyloxycarbonyl-S-methyl-L-penicillaminyl)amido-1-[N-isoamyl-N-(tert-butylcarbamoyl)]amino-4-phenyl-2-butanol (850 mg, 1.43 mmol) in dichloromethane (3.5 mL) was added 4N HCl in dioxane (2.4 mL). The reaction was stirred for 75 minutes, then concentrated to a white foam, 760 mg (100%). Used as is in the next reaction.
Step C: (2R, 3S)-3-(N-chloroacetyl-S-methyl-L-penicillaminyl) amido-1-[N-isoamyl-N-(tert-butylcarbamoyl)]amino-4-phenyl-2-butanol To a solution of (2R, 3S)-3-(S-methyl-L-penicillaminyl) amido-1-[N-isoamyl-N-(tert-butylcarbamoyl)]amino-4-phenyl-2-butanol hydrochloride (660 mg, 1.24 mmol) and diisopropylethylamine (320 µL, 1.87 mmol) in dichloromethane (10 mL) at 0° C. was added chloroacetic anhydride (290 mg, 1.71 mmol). The reaction was brought to room temperature and stirred for 45 minutes. The solvent was removed on a rotary evaporator and the residue partitioned between ethyl acetate (50 mL) and 1% citric acid solution (50 mL). The organic solution was washed with saturated NaHCO$_3$ solution (50 mL), saturated NaCl solution (50 mL) and dried (Na$_2$SO$_4$). Filtration and concentration gave a white foam, 700 mg (99%).

Step D: (2R, 3S)-3-(N-methylaminoacetyl-S-methyl-L-penicillaminyl)amido-1-[N-isoamyl-N-(tert-butylcarbamoyl)]amino-4-phenyl-2-butanol To (2R, 3S)-3-(N-chloroacetyl-S-methyl-L-penicillaminyl) amido-1-[N-isoamyl-N-(tert-butylcarbamoyl)]amino-4-phenyl-2-butanol (220 mg, 0.38 mmol) in isopropanol (5 mL) was added 40% aqueous methylamine (0.4 mL, 4.6 mmol). The reaction was stirred for 48 hours at room temperature, then concentrated on a rotary evaporator. The residue was taken up in ethyl acetate (20 mL) and washed with water, saturated NaHCO$_3$, and saturated NaCl (20 mL each), then dried (Na$_2$SO$_4$). The solvent was removed to give a white foam (202 mg) which was purified by silica gel chromotography using 2% methanol/dichlorlmethane as the eluting solvent, 97 mg (45%). Anal. Calc'd for; C$_{29}$H$_{51}$N$_5$O$_4$S 0.5 H$_2$O: C, 60.59; H, 9.12; N, 12.18. Found; C, 60.43; H, 9.09; N, 12.16.

PART II
(2R, 3S)-3-(N,N-dimethylaminoacetyl-S-methyl-L-penicillaminyl) amido-1-[N-isoamyl-N-(tert-butylcarbamoyl)]amino-4-phenyl-2-butanol To (2R, 3S)-3-(N-chloroacetyl-S-methyl-L-penicillaminyl)amido-1-[N-isoamyl-N-(tert-butylcarbamoyl)]amino-4-phenyl-2-butanol (220 mg, 0.38 mmol) in isopropanol (5 mL) was added 40% aqueous dimethylamine (0.5 mL, 3.9 mmol). The reaction was stirred for 3 hours at room temperature, then concentrated on a rotary evaporator. The residue was taken up in ethyl acetate (20 mL) and washed with water, saturated NaHCO$_3$, and saturated NaCl (20 mL each), then dried (Na$_2$SO$_4$). The solvent was removed to give a white foam which was purified by silica gel chromatography using 3% methanol/dichlorlmethane as the eluting solvent, 101 mg (46%). Anal. Calc'd for; C$_{30}$H$_{53}$N$_5$O$_4$S 0.3 H$_2$O: C, 61.46; H, 9.39; N, 11.94. Found; C, 61.40; H, 9.56; N, 11.99.

Example 6
(2R, 3S)-3-(N-methylaminoacetyl-L-tert-butylglycinyl)amido-1-[N-isoamyl-N-(tert-butylcarbamoyl)]amino-4-phenyl-2-butanol methanesulfonate To a solution of (2R, 3S)-3(N-methylaminoacetyl-L-tert-butylglycinyl)amido-1-[N-isoamyl-N-(tert-butylcarbamoyl)]amino-4-phenyl-2-butanol (497 mg, 0.9 mmol) in dichloromethane (10 mL) was added methanesulfonic acid (61 uL, 0.9 mmol). The solution was concentrated and the residue taken up in acetonitrile (2.5 mL). To this was added diethyl ether (20 mL). The product appeared as an oil. The ether was decanted and replaced with fresh ether (20 mL) and the oil triturated. A white solid formed. The ether was again decanted and replaced and the solid triturated overnight. The solid was collected by suction filtration, washed with ether and dried in-vacuo, 377 mg (64%). 1H NMR (CDCl3) ∂ 0.85 (s, 9H, t-Bu), 0.95 (dd, 6H, i-amyl), 1.37 (s, 9H, t-Bu), 2.83 (s, 3H, MeSO3-), 2.88 (bs, 3H, NMe), 7.30 (m,5H, ArH).

Consistent with more preferred general procedure above describing the preparation of the epoxide intermediate, the following Examples 7–9 exemplify the more preferred method of preparing the N,N, alpha-S-Tris(phenylmethyl)-2S-oxiranemethanamine, useful as an intermediate in the described general procedure.

Example 7
β-2-[Bis(phenylmethyl)amino]benzenepropanol
METHOD 1
Step 1: Benzylation of L-Phenylalanine A solution of L-phenylalanine (50.0 g, 0.302 mol), sodium hydroxide (24.2 g, 0.605 mol) and potassium carbonate (83.6 g, 0.605 mol) in water (500 mL) was heated to 97° C. Benzyl bromide (108.5 mL, 0.605 mol) was then slowly added (addition time −25 min). The mixture was stirred at 97° C. for 30 minutes under a nitrogen atmosphere. The solution was cooled to room temperature and extracted with toluene (2×250 mL). The combined organic layers were washed with water and brine, dried over magnesium sulfate, filtered and concentrated to an oil. The identity of the product was confirmed as follows. Analytical TLC (10% ethyl acetate/hexane, silica gel) showed major component at Rf value=0.32 to be the desired tribenzylated compound, N,N-bis(phenylmethyl)-L-phenylalanine phenylmethyl ester. This compound can be purified by column chromatography (silica gel, 15% ethyl acetate/hexanes). Usually the product is pure enough to be used directly in the next step without further purification. 1H NMR spectrum was in agreement with published literature. 1H NMR (CDCL3) ∂, 3.00 and 3.14 (ABX-system, 2H, JAB=14.1 Hz, JAX=7.3 Hz and JBX=5.9 Hz), 3.54 and 3.92 (AB-System, 4H, JAB=13.9 Hz),3.71 (t, 1H, J=7.6 Hz), 5.11 and 5.23 (AB-System, 2H, JAB=12.3 Hz), and 7.18 (m, 20 H). EIMS: m/z 434 (M-1).

Step 2: βS-2-[Bis(phenylmethyl)amino]benzenepropanol from the DIBAL Reduction of N,N-bis(phenylmethyl)-L-Phenylalanine phenylmethyl ester The benzylated phenylalanine phenylmethyl ester (0.302 mol) from the previous reaction was dissolved in toluene (750 mL) and cooled to −55° C. A 1.5M solution of DIBAL in toluene (443.9 mL, 0.666 mol) was added at a rate to maintain the temperature between −55° to −50° C. (addition time −1 hr). The mixture was stirred for 20 minutes under a nitrogen atmosphere and then quenched at −55° C. by the slow addition of methanol (37 ml). The cold solution was then poured into cold (5° C.) 1.5N HCl solution (1.8 L). The precipitated solid (approx. 138 g) was filtered off and washed with toluene. The solid material was suspended in a mixture of toluene (400 mL) and water (100 ml). The mixture was cooled to 5° C. and treated with 2.5N NaOH (186 mL) and then stirred at room temperature until solid dissolved. The toluene layer was separated from the aqueous phase and washed with water and brine, dried over magnesium sulfate, filtered and concentrated to a volume of 75 mL (89 g). Ethyl acetate (25 mL) and hexane (25 mL) were added to the residue upon which the desired alcohol product began to crystallize. After 30 min, an additional 50 mL hexane were added to promote further crystallization. The solid was filtered off and washed with 50 mL hexane to give 34.9 g of first crop product. A second crop of product (5.6 g) was isolated by refiltering the mother liquor. The two crops were combined and recrystallized from ethyl acetate (20 mL) and hexane (30 mL) to give 40 g of βS2-[Bis (phenylmethyl)amino]benzenepropanol, 40% yield from L-phenylalanine. An additional 7 g (7%) of product can be obtained from recrystallization of the concentrated mother liquor. TLC of product Rf=0.23 (10% ethyl acetate/hexane, silica gel);1H NMR (CDCl3) ∂ 2.44 (m, 1H,), 3.09 (m, 2H), 3.33 (m, 1H), 3.48 and 3.92 (AB-System, 4H, JAB=13.3 Hz), 3.52 (m, 1H) and 7.23 (m, 15H); [a]D25 +42.4 (c 1.45, CH2Cl2); DSC 77.67° C.; Anal. Calcd. for C23H25ON: C, 83.34; H. 7.60; N. 4.23. Found: C. 83.43; H. 7.59; N. 4.22. HPLC on chiral stationary phase: Cyclobond I SP column (250×4.6 mm I.D.), mobile phase: methanol/triethyl ammonium acetate buffer pH 4.2 (58:42, v/v), flow-rate of 0.5 ml/min, detection with detector at 230 nm and a temperature of 0° C. Retention time: 11.25 min., retention time of the desired product enantiomer: 12.5 min.

METHOD 2
Preparation of βS-2-[Bis(phenylmethyl)amino]benzenepropanol from the N,N-Dibenzylation of L-Phenylalaninol L-phenylalaninol (176.6 g, 1.168 mol) was added to a stirred solution of potassium carbonate (484.6 g, 3.506 mol) in 710 mL of water. The mixture was heated to 65° C. under a nitrogen atmosphere. A solution of benzyl bromide (400 g, 2.339 mol) in 3A ethanol (305 mL) was added at a rate that maintained the temperature between 60°–68° C. The biphasic solution was stirred at 65° C. for 55 min and then allowed to cool to 10° C. with vigorous stirring. The oily product solidified into small granules. The product was diluted with 2.0 L of tap water and stirred for 5 minutes to dissolve the inorganic by products. The product was isolated by filtration under reduced pressure and washed with water until the pH is 7. The crude product obtained was air dried overnight to give a semi-dry solid (407 g) which was recrystallized from 1.1 L of ethyl acetate/heptane (1:10 by volume). The product was isolated by filtration (at –8° C.), washed with 1.6 L of cold (–10° C.) ethyl acetate/heptane (1:10 by volume) and air-dried to give 339 g (88% yield) of βS-2-[Bis(phenylmethyl)amino]benzene-propanol, mp 71.5°– 73.0° C. More product can be obtained from the mother liquor if necessary. The other analytical characterization was identical to compound prepared as described in Method 1.

Example 8
alpha-S-[Bis(phenylmethyl)amino]benzenepropanaldehyde
METHOD 1

βS-2-[Bis(phenylmethyl)amino]benzene-propanol (200 g, 0.604 mol) was dissolved in triethylamine (300 mL, 2.15 mol). The mixture was cooled to 12° C. and a solution of sulfur trioxide/pyridine complex (380 g, 2.39 mol) in DMSO (1.6 L) was added at a rate to maintain the temperature between 8°–17° C. (addition time –1.0 h). The solution was stirred at ambient temperature under a nitrogen atmosphere for 1.5 hours at which time the reaction was complete by TLC analysis (33% ethyl acetate/hexane, silica gel). The reaction mixture was cooled with ice water and quenched with 1.6 L of cold water (10°–15° C.) over 45 minutes. The resultant solution was extracted with ethyl acetate (2.0 L), washed with 5% citric acid (2.0 L), and brine (2.2 L), dried over MgSO4 (280 g) and filtered. The solvent was removed on a rotary evaporator at 35°–40° C. and then dried under vacuum to give 198.8 g of alpha-S-[Bis-(phenylmethyl)amino]benzenepropanaldehyde as a pale yellow oil (99.9%). The crude product obtained was pure enough to be used directly in the next step without purification. The analytical data of the compound were consistent with the published literature.[alpha]$_D$25=–92.9° (c 1.87, $CH_2Cl_2$); 1H NMR (400 MHz, CDCl3) delta, 2.94 and 3.15 (ABX-System, 2H, JAB=13.9 Hz, JAX=7.3 Hz and JBX=6.2 Hz), 3.56 (t, 1H, 7.1 Hz), 3.69 and 3.82 (AB-System, 4H, JAB=13.7 Hz), 7.25 (m, 15H) and 9.72 (s, 1H); HRMS calcd for (M+1) C23H24NO 330.450, found: 330.1836. Anal. Calcd. for C23H23ON: C, 83.86; H, 7.04; N, 4.25. Found: C, 83.64; H, 7.42; N, 4.19. HPLC on chiral stationary phase:(S,S) Pirkle-Whelk-O 1 column (250×4.6 mm I.D.), mobile phase: hexane/isopropanol (99.5:0.5, v/v), flow-rate: 1.5 ml/min, detection with UV detector at 210 nm. Retention time of the desired S-isomer: 8.75 min., retention time of the R-enanatiomer 10.62 min.

METHOD 2

A solution of oxalyl chloride (8.4 ml, 0.096 mol) in dichloromethane (240 ml) was cooled to –74° C. A solution of DMSO (12.0 ml, 0.155 mol) in dichloromethane (50 ml) was then slowly added at a rate to maintain the temperature at –74° C. (addition time ~1.25 hr). The mixture was stirred for 5 min. followed by addition of a solution of the alcohol (0.074 mol) in 100 ml of dichloromethane (addition time –20 min., temp. –75° C. to –68° C.). The solution was stirred at –78° C. for 35 minutes under a nitrogen atmosphere. Triethylamine (41.2 ml, 0.295 mol) was then added over 10 min. (temp. –78° to –68° C.) upon which the ammonium salt precipitated. The cold mixture was stirred for 30 min. and then water (225 ml) was added. The dichloromethane layer was separated from the aqueous phase and washed with water, brine, dried over magnesium sulfate, filtered and concentrated. The residue was diluted with ethyl acetate and hexane and then filtered to further remove the ammonium salt. The filtrate was concentrated to give the desired aldehyde product. The aldehyde was carried on to the next step without purification.

Example 9
N,N-alpha-S-Tris(phenylmethyl)-2S-oxiranemethanamine
METHOD 1

A solution of alpha-S-[Bis(phenylmethyl)amino]benzene-propanaldehyde (191.7 g, 0.58 mol) and chloroiodomethane (56.4 mL, 0.77 mol) in tetrahydrofuran (1.8 L) was cooled to –30° to –35° C. (colder temperature such as –70° C. also worked well but warmer temperatures are more readily achieved in large scale operations) in a stainless steel reactor under a nitrogen atmosphere. A solution of n-butyllithium in hexane (1.6M, 365 mL, 0.58 mol) was then added at a rate that maintained the temperature below –25° C. After addition the mixture was stirred at –30° to –35° C. for 10 minutes. More additions of reagents were carried out in the following manner: (1) additional chloroiodomethane (17 mL) was added, followed by n-butyllithium (110 mL) at <–25° C. After addition the mixture was stirred at –30° to –35° C. for 10 minutes. This was repeated once. (2) Additional chloroiodomethane (8.5 mL, 0.11 mol) was added, followed by n-butyllithium (55 mL, 0.088 mol) at <–25° C. After addition the mixture was stirred at –30° to –35° C. for 10 minutes. This was repeated 5 times. (3) Additional chloroiodomethane (8.5 mL, 0.11 mol) was added, followed by n-butyllithium (37 mL, 0.059 mol) at <–25° C. After addition the mixture was stirred at –30° to –35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and theorganic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material. (The crude product weight was >100%. Due to the relative instability of the product on silica gel, the crude product is usually used directly in the next step without purification). The diastereomeric ratio of the crude mixture was determined by proton NMR: (2S)/(2R): 86:14. The minor and major epoxide diastereomers were characterized in this mixture by tlc analysis (silica gel, 10% ethyl acetate/hexane), Rf=0.29 & 0.32, respectively. An analytical sample of each of the diastereomers was obtained by purification on silica-gel chromatography (3% ethyl acetate/hexane) and characterized as follows:

N,N-alpha-S-Tris(phenylmethyl)-2S-oxiranemethanamine

1H NMR (400 MHz, CDCl3) delta 2.49 and 2.51 (AB-System, 1H, JAB=2.82), 2.76 and 2.77 (AB-System, 1H, JAB=4.03), 2.83 (m, 2H), 2.99 & 3.03 (AB-System, 1H, JAB=10.1 Hz), 3.15 (m, 1H), 3.73 & 3.84 (AB-System, 4H, JAB=14.00), 7.21 (m, 15H); 13C NMR (400 MHz, CDCl3) delta 139.55, 129.45, 128.42, 128.14, 128.09, 126.84, 125.97, 60.32, 54.23, 52.13, 45.99, 33.76; HRMS calcd for $C_{24}H_{26}NO$ (M+1) 344.477, found 344.2003.

N,N-alpha-S-Tris(phenylmethyl)-2R-oxiranemethanamine

1H NMR (300 MHz, CDCl3) delta 2.20 (m, 1H), 2.59 (m, 1H), 2.75 (m, 2H), 2.97 (m, 1H), 3.14 (m, 1H), 3.85 (AB-System, 4H), 7.25 (m, 15H).HPLC on chiral stationary phase: Pirkle-Whelk-O 1 column (250×4.6 mm I.D.), mobile phase: hexane/isopropanol (99.5:0.5, v/v), flow-rate: 1.5 ml/min, detection with UV detector at 210 nm. Retention time of(8): 9.38 min., retention time of enanatiomer of (4): 13.75 min.

METHOD 2

A solution of the crude aldehyde 0.074 mol and chloroiodomethane (7.0 ml, 0.096 mol) in tetrahydrofuran (285 ml) was cooled to –78° C., under a nitrogen atmosphere. A 1.6M solution of n-butyllithium in hexane (25 ml, 0.040 mol) was then added at a rate to maintain the temperature at –75° C. (addition time –15 min.). After the first addition, additional chloroiodomethane (1.6 ml, 0.022 mol) was added again, followed by n-butyllithium (23 ml, 0.037 mol), keeping the temperature at –75° C. The mixture was stirred for 15 min. Each of the reagents, chloroiodomethane (0.70 ml, 0.010 mol) and n-butyllithium (5 ml, 0.008 mol) were added 4 more times over 45 min. at –75° C. The cooling bath was then removed and the solution warmed to 22° C. over 1.5 hr. The mixture was poured into 300 ml of saturated aq. ammonium chloride solution. The tetrahydrofuran layer was separated. The aqueous phase was extracted with ethyl acetate (1×300 ml). The combined organic layers were washed with brine, dried over magnesium sulfate, filtered and concentrated to give a brown oil (27.4 g). The product could be used in the next step without purification. The desired diastereomer can be purified by recrystallization at a subsequent step. The product could also be purified by chromatography.

METHOD 3

A solution of alpha-S-[Bis(phenylmethyl)amino]benzenepropanaldehyde (178.84 g, 0.54 mol) and bromochloromethane (46 mL, 0.71 mol) in tetrahydrofuran (1.8 L) was cooled to –30° to –35° C. (colder temperature such as –70° C. also worked well but warmer temperatures are more readily achieved in large scale operations) in a stainless steel reactor under a nitrogen atmosphere. A solution of n-butyllithium in hexane (1.6M, 340 mL, 0.54 mol) was then added at a rate that maintained the temperature below –25° C. After addition the mixture was stirred at –30° to –35° C. for 10 minutes. More additions of reagents were carried out in the following manner: (1) additional bromochloromethane (14 mL) was added, followed by n-butyllithium (102 mL) at <–25° C. After addition the mixture was stirred at –30° to –35° C. for 10 minutes. This was repeated once. (2) Additional bromochloromethane (7 mL, 0.11 mol) was added, followed by n-butyllithium (51 mL, 0.082 mol) at <–25° C. After addition the mixture was stirred at –30° to –35° C. for 10 minutes. This was repeated 5 times. (3) Additional bromochloromethane (7 mL, 0.11 mol) was added, followed by n-butyllithium (51 mL, 0.082 mol) at <–25° C. After addition the mixture was stirred at –30° to –35° C. for 10 minutes. This was repeated once. The external cooling was stopped and the mixture warmed to ambient temp. over 4 to 16 hours when TLC (silica gel, 20% ethyl acetate/hexane) indicated that the reaction was completed. The reaction mixture was cooled to 10° C. and quenched with 1452 g of 16% ammonium chloride solution (prepared by dissolving 232 g of ammonium chloride in 1220 mL of water), keeping the temperature below 23° C. The mixture was stirred for 10 minutes and theorganic and aqueous layers were separated. The aqueous phase was extracted with ethyl acetate (2×500 mL). The ethyl acetate layer was combined with the tetrahydrofuran layer. The combined solution was dried over magnesium sulfate (220 g), filtered and concentrated on a rotary evaporator at 65° C. The brown oil residue was dried at 70° C. in vacuo (0.8 bar) for 1 h to give 222.8 g of crude material. The desired product may be obtained in a manner similar to methods 1 and 2 above.

Example 10

N-[3S-[bis(phenylmethyl)amino]-2R-hydroxy-4-phenylbutyl]-N'-(1,1-dimethylethyl)-N-(3-methylbutyl)urea To a solution of 168 g (0.489 mol) of crude epoxide, (N,N-alpha-S-tris(phenylmethyl)-2S-oxiranemethanamine as prepared in Example 9, in 290 mL of isopropanol, was added 290 mL of isoamylamine. The solution was refluxed for two hours, cooled and concentrated. The residue was dissolved in 670 mL of ethyl acetate, washed with water and then brine, dried over anhydrous magnesium sulfate, filtered and concentrated to afford 194.4 g of crude amino alcohol. This was dissolved in 1 L of ethyl acetate, cooled to 0° C. and 52 mL (0.45 mol) of tertiary-butyl isocyanate was added. The ice bath was removed and after stirring at room temperature for one hour, the solution was washed with 350 mL of 5% aqueous citric acid, 350 mL of saturated aqueous sodium bicarbonate and then 350 mL of saturated sodium chloride. The solution was dried over anhydrous magnesium sulfate, filtered and concentrated. The residue was dissolved in 300 mL of hot heptane, slowly cooled to room temperature and then to 0° C. The resulting tan solid was collected and washed with cold heptane to afford 107.5 g of the desired urea derivative, which was identified as N-[3S-[bis(phenylmethyl)amino]-2R-hydroxy-4-phenylbutyl]-N'-(1,1-dimethylethyl)-N-(3-methylbutyl)urea, mp 120°–122° C.

Example 11

(2R,3S)-3-Amino-1-isoamyl-1-(tert-butylcarbamoyl)amino-4-phenyl-2-butanol

A solution of N-[3S-[bis(phenylmethyl)amino]-2R-hydroxy-4-phenylbutyl]-N'-(1,1-dimethylethyl)-N-(3-methylbutyl)urea (147.0 g, 227 mmol), prepared according to the method of Example 10 above, in ethanol (1.47 L) and 20% palladium hydroxide-on-carbon (47.6 g) are placed in a 2.5 L Parr bottle and purged 5 times with nitrogen and 5 times with hydrogen. The hydrogen pressure is set at 60 psi and the reaction mixture is agitated on a Parr shaker for 6 hours. The catalyst is removed by filtration through a sintered glass funnel and concentrated to an off white foam. Final traces of solvent are removed in-vacuo to provide 98.3 g (101%) of (2R,3S)-3-amino-1-isoamyl-1-(tert-butylcarbamoyl)amino-4-phenyl-2-butanol, the compound of Example 2, Step E above.

Example 12

Following the methods of Example 2, the compounds of Table 1 were prepared from the appropriate corresponding starting materials:

TABLE 1

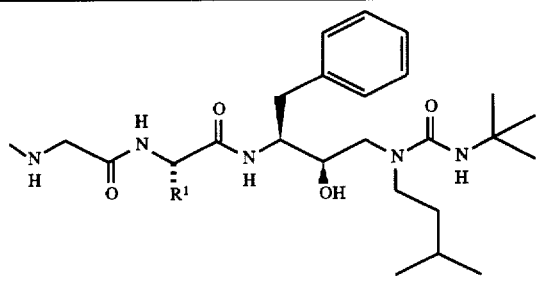

| Entry No. | R1 |
|---|---|
| 1 | —C(CH3)2(S[O]CH3) |
| 2 | —C(CH3)2 (S[O]2CH3) |
| 3 | —CH(CH3)2 |

Example 13

(2R, 3S)-3-(N-benzyloxycarbonyl-N-methyl-L-alaninyl-L-tert-butylglycinyl)amino-1-[N-isoamyl-N-(tert-butylcarbamoyl)]amino-4-phenyl-2-butanol To a solution of N-Cbz-N-methyl-L-alanine (237 mg; 1 mmol) in DMF (3 mL) was added HOBT (168 mg; 1.1 mmol). The solution was cooled to 0° C. and EDC (211 mg; 1.1 mmol) was added. After 45 minutes the product of Example 2, Step G above (446 mg; 1.0 mmol) in DMF (2 mL) was added and the reaction stirred at ambient temperature for 18 hours. The reaction was diluted with water (50 mL) and extracted with EtOAc (2×50 mL). The combined organic layers were washed with water (3×50 mL) and saturated NaCl solution (30 mL), then dried (MgSO4). The solution was concentrated on a rotary evaporator to a foam. The crude product was chromatographed on silica (50 gm) using 2% MeOH/CH2Cl2 as the eluting solvent. A white solid was obtained: 384 mg (56%). Analysis calculated for $C_{38}H_{59}N_5O_6 \cdot 0.5\ H_2O$: C, 66.06; H, 8.75; N, 10.14. Found: C, 66.02; H, 8.77; N, 10.39.

Example 14

(2R, 3S)-3-(N-methyl-L-alaninyl-L-tert-butylglycinyl)amino-1-[N-isoamyl-N-(tert-butylcarbamoyl)]amino-4-phenyl-2-butanol The product from Example 13 above (100 mg, 0.14 mmol) and 10% Pd on carbon (40 mg) were combined in MeOH (10 mL). To this was added ammonium formate (92 mg, 1.40 mmol) in water (1 mL). The reaction was stirred at ambient temperature for 18 hours. The reaction was filtered through diatomaceous earth and concentrated to a white solid. The solid was partitioned between EtOAc and saturated NaHCO3 (40 mL each). The EtOAc layer was extracted with saturated NaHCO3, water and saturated NaCl (20 mL each). The solution was dried (MgSO4) and concentrated to a white solid, 74 mg (96%). Analysis calculated for $C_{30}H_{53}N_5O_4$: C, 65.78; H, 9.75; N, 12.78. Found: C, 65.76; H, 9.99; N, 12.47.

Example 15

(2R, 3S)-3-(N-benzyloxycarbonyl-N-methyl-D-alaninyl-L-tert-butylglycinyl)amino-1-[N-isoamyl-N-(tert-butylcarbamoyl)]amino-4-phenyl-2-butanol To a solution of N-Cbz-N-methyl-D-alanine (178 mg; 0.75 mmol) in DMF (3 mL) was added HOBT (116 mg; 0.76 mmol). The solution was cooled to 0° C. and EDC (144 mg; 0.75 mmol) was added. After 45 minutes the product of Example 2, Step G above (312 mg; 0.7 mmol) in DMF (2 mL) was added and the reaction stirred at ambient temperature for 18 hours. The reaction was diluted with 50% saturated NaHCO3 solution (30 mL) and extracted with EtOAc (2≦30 mL). The combined organic layers were washed with saturated NaHCO3, water, 1N HCl, water, and saturated NaCl (30 mL each), then dried (MgSO4). The solution was concentrated on a rotary evaporator to an oil. The crude product was chromatographed on silica (50 gm) using 2% MeOH/CH2Cl2 as the eluting solvent. A white foam was obtained: 272 mg (57%). Analysis calculated for $C_{38}H_{59}N_5O_6 \cdot 0.3\ H_2O$: C, 66.41; H, 8.74; N, 10.19. Found: C, 66.45; H, 8.91; N, 10.11.

Example 16

(2R, 3S)-3-(N-methyl-D-alaninyl-L-tert-butylglycinyl)amino-1-[N-isoamyl-N-(tert-butylcarbamoyl)]amino-4-phenyl-2-butanol The product from Example 15 above (100 mg, 0.14 mmol) and 10% Pd on carbon (27 mg) was dissolved in 10:1 MeOH/H2O (8 mL). To this was added ammonium formate (92 mg, 1.40 mmol) in water (1 mL). The reaction was stirred at ambient temperature for 4 hours, then filtered through diatomaceous earth and concentrated to an oil. The oil was partitioned between EtOAc and saturated NaHCO3 (40 mL each). The EtOAc layer was extracted with saturated NaHCO3, water and saturated NaCl (40 mL each). The solution was dried (MgSO4) and concentrated to a colorless glass, 73 mg (95%). Analysis calculated for $C_{30}H_{53}N_5O_4 \cdot 0.2\ H_2O$: C, 65.35; H, 9.76; N, 12.70. Found: C, 65.26; H, 9.68; N, 12.34.

Example 17

(2R, 3S)-3-(N-tert-butoxycarbonyl-glycinyl-L-tert-butylglycinyl) amino-1-[N-isoamyl-N-(tert-butylcarbamoyl)]amino-4-phenyl-2-butanol To a solution of N-Boc-glycine (131 mg; 0.75 mmol) in DMF (3 mL) was added HOBT (116 mg; 0.76 mmol). The solution was cooled to 0° C. and EDC (144 mg; 0.75 mmol) was added. After 45 minutes the product of Example 2, Step G above (312 mg; 0.7 mmol) in DMF (2 mL) was added and the reaction stirred at ambient temperature for 18 hours. The reaction was diluted with 50% saturated NaHCO3 solution (35 mL) and extracted with EtOAc (2×30 mL). The combined organic layers were washed with saturated NaHCO3, water, 5% citric acid, water, and saturated NaCl (30 mL each), then dried (MgSO4). The solution was concentrated on a rotary evaporator to a foam. The crude product was chromatographed on silica (50 gm) using 2% MeOH/CH2Cl2 as the eluting solvent. A white foam was obtained: 270 mg (43%). Analysis calculated for $C_{33}H_{57}N_5O_6 \cdot 0.2\ H_2O$: C, 63.58; H, 9.28; N, 11.23. Found: C, 63.52; H, 9.06; N, 10.97.

Example 18

(2R, 3S)-3-(glycinyl-L-tert-butylglycinyl)amino-1-[N-isoamyl-N-(tert-butylcarbamoyl)]amino-4-phenyl-2-butanol Hydrochloride Salt To a CH2Cl2 (2 mL) solution of the product of Example 17 above was added 4N HCl in dioxane (2 mL). The reaction was stirred at ambient temperature for 1 hour then concentrated to a solid. The solid was chased with MeOH, then CH2Cl2. The solid was taken up in CH2Cl2 and filtered through a 0.45 micron PTFE filter disc. The solvent was evaporated and the resulting solid dried in-vacuo, 73 mg (82%). Analysis calculated for $C_{28}H_{50}N_5O_4Cl.1.25\ H_2O$: C, 58.11; H, 9.14; N, 12.10. Found: C, 58.25; H, 8.84; N, 11.71.

Example 19
(2R, 3S)-3-(N-benzyloxycarbonyl-L-prolyl-L-tert-butylglycinyl) amino-1-[N-isoamyl-N-(tert-butylcarbamoyl)]amino-4-phenyl-2-butanol To a solution of N-Cbz-L-proline (119 mg; 0.48 mmol) in DMF (4 mL) was added HOBT (61 mg; 0.46 mmol) and EDC (87 mg; 0.46 mmol). After 45 minutes the product of Example 2, Step G above (200 mg; 0.43 mmol) in DMF (4 mL) was added and the reaction stirred at ambient temperature for 18 hours. The reaction was concentrated and the residue taken up in EtOAc (30 mL). The solution was washed with 1N HCl, saturated $NaHCO_3$ and saturated NaCl (30 mL each), then dried $(Na_2SO_4)$. The solution was concentrated on a rotary evaporator to a foam, 237 mg (80%). The product was identified by its NMR spectrum.

Example 20
(2R, 3S)-3-(L-prolyl-L-tert-butylglycinyl)amino-1-[N-isoamyl-N-(tert-butylcarbamoyl)]amino-4-phenyl-2-butanol The product of Example 19 above (205 mg, 0.3 mmol) was dissolved in MeOH (15 mL) and to this was added 10% Pd on carbon. The mixture was hydrogenated at 5 psi of hydrogen at ambient temperature for 4 hours. The reaction mixture was filtered through diatomaceous earth and concentrated to a gummy solid, 160 mg (95%). The product was identified by its NMR spectrum.

Following the procedures of Examples 19 and 20, the corresponding D-prolyl compound can also be prepared.

Example 21
(2R, 3S)-3-(N-tert-butoxycarbonyl-L-prolyl-L-tert-butylglycinyl) amino-1-[N-isoamyl-N-(tert-butylcarbamoyl)]amino-4-phenyl-2-butanol To a solution of N-Boc-L-proline (104 mg; 0.48 mmol) in DMF (5 mL) was added HOBT (62 mg; 0.46 mmol) and EDC (89 mg; 0.46 mmol). After 45 minutes the product of Example 2, Step G above (200 mg; 0.43 mmol) in DMF (3 mL) was added and the reaction stirred at ambient temperature for 18 hours. The reaction was concentrated and the residue taken up in EtOAc (30 mL). The solution was washed with 1N HCl, saturated $NaHCO_3$ and saturated NaCl (30 mL each), then dried $(Na_2SO_4)$. The solution was concentrated on a rotary evaporator to a foam, 185 mg (65%). The product was identified by its NMR spectrum and combustion analysis. Analysis calculated for $C_{36}H_{61}N_5O_6$.0.5 $H_2O$: C, 64.64; H, 9.34; N, 10.47. Found: C, 64.44; H, 9.10; N, 10.76.

Example 22
(2R, 3S)-3-(N-benzyloxycarbonyl-N-methyl-D-alaninyl-L-isoleucinyl)amino-1-[N-isoamyl-N-(tert-butylcarbamoyl)] amino-4-phenyl-2-butanol To a solution of N-Cbz-N-methyl-D-alanine (115 mg; 0.48 mmol) in DMF (3 mL) was added HOBT (62 mg; 0.46 mmol). The solution was cooled to 0° C. and EDC (89 mg; 0.46 mmol) was added. After 45 minutes the free base of the product of Example 4, Step B above (200 mg; 0.43 mmol) in DMF (3 mL) was added and the reaction stirred at ambient temperature for 3 hours. The reaction was concentrated and the residue dissolved in EtOAc (30 mL). The organic solution was washed with 1N HCl, saturated $NaHCO_3$, and saturated NaCl (30 mL each), then dried $(Na_2SO_4)$. The solution was concentrated on a rotary evaporator to a white solid, 258 mg (87%). The product was identified by its NMR spectrum.

Example 23
(2R, 3S)-3-(N-methyl-D-alaninyl-L-isoleucinyl)amino-1-[N-isoamyl-N-(tert-butylcarbamoyl)]amino-4-phenyl-2-butanol The product from Example 22 above (258 mg, 0.38 mmol) and 10% Pd on carbon (26 mg) was dissolved in MeOH (10 mL). The reaction was hydrogenated at 5 psi at ambient temperature for 3 hours. The reaction was filtered through diatomaceous earth and concentrated to a foam. The solid was chromatographed on silica (50 gm) using 2% $MeOH/CH_2Cl_2$ as the eluting solvent. The solvent was concentrated to give a white solid, 190 mg (91%). Analysis calculated for $C_{30}H_{53}N_5O_4.0.3\ H_2O$: C, 65.13; H, 9.76; N, 12.66. Found: C, 64.85; H, 9.84; N, 12.24.

Example 24
(2R, 3S)-3-(N-benzyloxycarbonyl-L-prolyl-L-isoleucinyl) amino-1-[N-isoamyl-N-(tert-butylcarbamoyl)]amino-4-phenyl-2-butanol To a solution of N-Cbz-L-proline (121 mg; 0.48 mmol) in DMF (3 mL) was added HOBT (62 mg; 0.46 mmol) and EDC (87 mg; 0.46 mmol). After 45 minutes the free base of the product of Example 4, Step B above (200 mg; 0.43 mmol) in DMF (5 mL) was added and the reaction stirred at ambient temperature for 4 hours. The reaction was concentrated and the residue dissolved in EtOAc (30 mL). The organic solution was washed with 1N HCl, saturated $NaHCO_3$, and saturated NaCl (30 mL each), then dried $(Na_2SO_4)$. The solution was concentrated on a rotary evaporator to a white solid, 266 mg (89%). The product was identified by its NMR spectrum.

Example 25
(2R, 3S)-3-(L-prolyl-L-isoleucinyl)amino-1-[N-isoamyl-N-(tert-butylcarbamoyl)]amino-4-phenyl-2-butanol The product from Example 24 above (266 mg, 0.38 mmol) and 10% Pd on carbon (26 mg) was dissolved in MeOH (10 mL). The reaction was hydrogenated at 5 psi at ambient temperature for 2 hours. The reaction was filtered through diatomaceous earth and concentrated to an foam, 202 mg (95%). Analysis calculated for $C_{31}H_{53}N_5O_4.0.5\ H_2O$: C, 65.46; H, 9.57; N, 12.31. Found: C, 65.34; H, 9.97; N, 12.25.

Following the procedures of Examples 24 and 25, the corresponding D-prolyl compound can also be prepared.

Example 26
(2R, 3S)-3-(N-benzyloxycarbonyl-L-isoleucinyl-L-isoleucinyl)amino-1-[N-isoamyl-N-(tert-butylcarbamoyl)] amino-4-phenyl-2-butanol To N-Cbz-L-isoleucine hydroxysuccinimide ester (109 mg; 0.30 mmol) was added the free base of the product of Example 4, Step B above (200 mg; 0.43 mmol) in DMF (12 mL) and the reaction stirred at ambient temperature for 18 hours. The reaction was concentrated and the residue dissolved in EtOAc (30 mL). The organic solution was washed with saturated $NaHCO_3$ (30 mL), then dried $(Na_2SO_4)$. The solution was concentrated on a rotary evaporator to a white solid, 168 mg (79%). The product was identified by its NMR spectrum.

Example 27
Butaneamide, 2-[(N-methylaminoacetyl)amino]-N-[3-[[[(1,1-dimethylethyl)amino]carbonyl](3-methylbutyl)amino]-2-hydroxy-1-(phenylmethyl)propyl]-3,3-dimethyl-, [1S-[1R*(R*), 2S*]]-

Butaneamide, 2-[(N,N-dimethylaminoacetyl)amino]-N-[3-[[[(1,1-dimethylethyl)amino]carbonyl](3-methylbutyl)amino]-2-hydroxy-1-(phenylmethyl)propyl]-3,3-dimethyl-, [1S-[1R*(R*), 2S*]]-, as prepared in Example 1 herein, is administered to male rats (n=5) orally in water containing 0.5% methylcellulose and 0.1% polysorbate 80 in a total volume of 5 to 7 mL per kilogram. Blood samples are collected at 0.25, 0.50, 1, 2 and 4 hours. The samples for each time-point are pooled and extracted onto a 100 mg $C_{18}$ solid phase extraction column (SPEC) after prior treatment with methanol to denature plasma proteins. The extract is purified by washing the SPEC with water and collected after the addition of 1% formic acid in methanol to the SPEC. Concentration of the extract is achieved by evaporation and resolubilization in a small volume of water:acetonitrile (3:1, v/v). The resolubilized extract is filtered through a 0.2μ filter and injected onto a liquid chromatograph coupled to a mass spectrometer, using a VG Trio 2 Mass Spectrometer, by means of a thermospray interface. The chromatographic separation is produced by use of a 10 cm (2×5 cm) YMC Basic column with a mobile phase of water:acetonitrile:pyridine:formic acid (545:440:10:5, by volume). Data are obtained for which the corresponding spectra and chromatogram from a standard of the synthesized metabolite can be favorably compared.

Example 28

The compounds of the present invention are advantageously effective HIV protease inhibitors. Utilizing an enzyme assay as described below, the compounds set forth in the examples herein disclosed inhibited the HIV enzyme. The preferred compounds of the present invention and their calculated IC50 (the concentration at which the inhibitor compound reduces enzyme activity by 50%) values are shown in Table 2.

The enzyme method is as follows. The substrate is 2-aminobenzoyl-Ile-Nle-Phe(p-NO2)-Gln-ArgNH2. The positive control is MVT-101 (Miller, M. et al, Science, 246, 1149 (1989)). The assay buffer is 20 mM sodium phosphate, pH 6.4, 20% glycerol, 1 mM EDTA, 1 mM DTT and 0.1% CHAPS. The substrate is dissolved in DMSO, then diluted 10 fold in assay buffer. Final substrate concentration in the assay is about 80 μM. HIV protease is diluted in the assay buffer to a final enzyme concentration of about 12.3 nanomolar, based on a molecular weight of 10,780.

The final concentration of DMSO is about 14% and the final concentration of glycerol is about 18%. The test compound is dissolved in DMSO and diluted in DMSO to ten times (10×) the test concentration. Ten microliters (10 μL) of the enzyme preparation is added, the materials mixed and then the mixture is incubated at ambient temperature for 15 minutes. The enzyme reaction is initiated by the addition of 40 μL of substrate. The increase in fluorescence is monitored at 4 time points (0, 8, 16 and 24 minutes) at ambient temperature. Each assay is carried out in duplicate wells.

Example 29

The effectiveness of selected compounds of the present invention were determined in the above-described enzyme assay and in a CEM cell assay.

The HIV inhibition assay method of acutely infected cells is an automated tetrazolium based calorimetric assay essentially that reported by Pauwles et al, J. Virol. Methods 20, 309–321 (1988). Assays were performed in 96-well tissue culture plates. CEM cells, a CD4+ cell line, were grown in RPMI-1640 medium (Gibco) supplemented with a 10% fetal calf serum and were then treated with polybrene (2 μg/ml). An 80 μl volume of medium containing 1×104 cells was dispensed into each well of the tissue culture plate. To each well was added a 100 μl volume of test compound dissolved in tissue culture medium (or medium without test compound as a control) to achieve the desired final concentration and the cells were incubated at 37° C. for 1 hour. A frozen culture of HIV-1 was diluted in culture medium to a concentration of 5×104 TCID50 per ml (TCID50=the dose of virus that infects 50% of cells in tissue culture), and a 20 μL volume of the virus sample (containing 1000 TCID50 of virus) was added to wells containing test compound and to wells containing only medium (infected control cells). Several wells received culture medium without virus (uninfected control cells). Likewise, the intrinsic toxicity of the test compound was determined by adding medium without virus to several wells containing test compound. In summary, the tissue culture plates contained the following experiments:

|   | Cells | Drug | Virus |
|---|-------|------|-------|
| 1. | + | − | − |
| 2. | + | + | − |
| 3. | + | − | + |
| 4. | + | + | + |

In experiments 2 and 4 the final concentrations of test compounds were 1, 10, 100 and 500 μg/ml. Either azidothymidine (AZT) or dideoxyinosine (ddI) was included as a positive drug control. Test compounds were dissolved in DMSO and diluted into tissue culture medium so that the final DMSO concentration did not exceed 1.5% in any case. DMSO was added to all control wells at an appropriate concentration.

Following the addition of virus, cells were incubated at 37° C. in a humidified, 5% $CO_2$ atmosphere for 7 days. Test compounds could be added on days 0, 2 and 5 if desired. On day 7, post-infection, the cells in each well were resuspended and a 100 μl sample of each cell suspension was removed for assay. A 20 μL volume of a 5 mg/ml solution of 3-(4,5-dimethylthiazol-2-yl)-2,5-diphenyltetrazolium bromide (MTT) was added to each 100 μL cell suspension, and the cells were incubated for 4 hours at 27° C. in a 5% $CO_2$ environment. During this incubation, MTT is metabolically reduced by living cells resulting in the production in the cell of a colored formazan product. To each sample was added 100 μl of 10% sodium dodecylsulfate in 0.01N HCl to lyse the cells, and samples were incubated overnight. The absorbance at 590 nm was determined for each sample using a Molecular Devices microplate reader. Absorbance values for each set of wells is compared to assess viral control infection, uninfected control cell response as well as test compound by cytotoxicity and antiviral efficacy.

TABLE 2

| Compound of Example No. | $IC_{50}$ (nM) | $EC_{50}$ | $TD_{50}$ |
|---|---|---|---|
| 1 | 10 | 58 nM | 45,000 |
| 2 | 6 | 22 nM | 45,000 |
| 3 | 14 | 66 nM | |
| 4 | 13 | 91 nM | 55,000 |
| 5 (Part I) | 14 | | |
| 13 | 14 | 34 ng/mL | |

TABLE 2-continued

| Compound of Example No. | IC$_{50}$ (nM) | EC$_{50}$ | TD$_{50}$ |
|---|---|---|---|
| 14 | 8 | 96 ng/mL | |
| 15 | 70 | | |
| 16 | 18 | 59 ng/mL | |
| 17 | 10 | | |
| 18 | 10 | 38 ng/mL | |
| 19 | 2200 | | |
| 20 | 9 | | |
| 21 | 61% @ 10 µM | | |
| 22 | 370 | | |
| 23 | 79 | | |
| 24 | 520 | | |
| 25 | 51 | | |

The compounds of the present invention are advantageously effective antiviral compounds and, in particular, are effective inhibitors of retroviruses, particularly, lentiviruses as shown above. Thus, the subject compounds are effective inhibitors of HIV. It is contemplated that the subject compounds will also inhibit other strains of HIV, such as HIV-2 and other viruses such as, for example, VIS-A virus and Simian Immunodeficiency virus (SIV), HTLV-1 and HTLV-2. Thus, the subject compounds are effective in the treatment and/or prophylaxis of retroviral infections.

Compounds of the present can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomericaly pure compound. The optically active compounds of Formula I can likewise be obtained by utilizing optically active starting materials. These isomers may be in the form of a free acid, a free base, an ester or a salt.

The present invention is also meant to include the solvate or hydrates of the compounds of the formula I, when possible, and are prepared or isolated by methods known in the art.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid preferably hydrochloride salt. Other examples include salts with alkali metals or alkaline earth metals, such as sodium, potassium, calcium or magnesium or with organic bases. Total daily dose administered to a host in single or divided doses may be in amounts, for example, from 0.01 to 50 mg/kg body weight daily and more usually 0.1 to 30 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore may deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with two or three other antiviral agents which are effective against HIV-1. Such compounds include, but are not limited to; other HIV-1 protease inhibitors as disclosed in co-owned and co-filed with this application U.S. patent application Ser. No. 08/253,638, now abandoned incorporated herein by reference in its entirety, various nucleoside analogs nonnucleoside reverse transcriptase inhibitors, tat antagonists and glycosidase inhibitors.

Examples of HIV-1 protease inhibitors include, but not limited to, Ro 31-8959 (Roberts, N. A. et al. Science 1990, 248, 358–361 and Drugs of the Future 1991, 16(3), 210–212), KNI-272, (Kagayama, S., et al. Antimicrobial Agents and Chemotherapy 1993, 810–817), the cyclic urea series (Lam, P., et al., "De Novo Design and Discovery of Potent, Nonpeptidal HIV-1 Protease Inhibitors," paper 96 at the 205th American Chemical Society National Meeting, Medicinal Chemistry Division, Denver, Colo., Mar. 28–Apr. 2, 1993), L-735,524 (Dorsey, B. D., et al., "L-735,524: The Rational Design of a Potent and Orally Bioavailable HIV Protease Inhibitor," paper 6 at the 206th American Chemical Society National Meeting, Medicinal Chemistry Division, Chicago, Ill., Aug. 22–27, 1993) and analogs thereof. Additional examples include V. Kalish, "Lead Optimization Utilizing Iterative Protein Structure-Based Drug Design: Potent, Orally Bioavailable HIV Protease Inhibitors," 35th Annual Buffalo Medicinal Chemistry Meeting, State University of New York at Buffalo, Buffalo, N.Y., May 22–25, 1994; and S. Thaisrivongs, "Structure-Based Design of Non-Peptide HIV Protease Inhibitors," 35th Annual Buffalo Medicinal Chemistry Meeting, State University of New York at Buffalo, Buffalo, N.Y., May 22–25, 1994.

Examples of competitive nucleoside analogs include, but are not limited to, AZT, DDI, DDC, 3TC, D4T and PMEA. Examples of non-nucleoside, non-competitive reverse transcriptase inhibitors include, but are not limited to, the pyridone class (Wei, J. S., et al. J. Med. Chem. 1993, 36, 249–255; Hoffman, J. M., et al. J. Med. Chem. 1992, 35, 3784–3791; Saari et al. J. Med. Chem. 1992, 35 3792–3802; Drugs of the Future 1992, 17(4), 283–285, and analogs thereof); the bis-(heteroaryl)piperazines class (Romero, D. L., et al. J. Med. Chem. 1993, 36, 1505–1508; Romero, D. L., et al. Proc. Natl. Acad. Sci. USA 1991, 34, 746–751 and 3187–3198; and analogs thereof) and the tricyclic pyridobenzo- and depyridodiazepinones (Hargrave, K. D., J. Med. Chem. 1991, 34, 2231–2241; Merluzzi, M. J. Science 1990, 250, 1411–1413; and analogs thereof) and 5-chloro-3-(phenylsulfonyl)indole-2-carboxamide and its analogs (Williams, T. M. et al., J. Med. Chem. 1993, 36, 1291–1294). Examples of tat antagonists include, but are not limited to, Ro 5-3335 and Ro 24-7429 (Hsu, M. C. et al., Proc. Natl. Acad. Sci. USA 1993, 909, 6395–6399; Tam, S. et al., "TAT INHIBITORS: A NEW CLASS OF ANTI-HIV AGENTS," paper 372, at the 204th American Chemical Society National Meeting, Organic Chemistry Division, Washington, D.C., Aug. 23–28, 1992) and analogs thereof. Examples of glycosidase inhibitors include, but are not limited to, castanospermine, castanospermine 6-butryl ester, N-butyl-1-deoxynojirimycin, N-butyl-1-deoxynojirimycin per-butryl ester and analogs and prodrugs thereof.

When administered as a combination, the therapeutic agents can be formulated as separate compositions which are given at the same time or different times, or the therapeutic agents can be given as a single composition.

The compounds of the present invention are effective antiviral compounds and, in particular, are effective retroviral inhibitors as shown above. Thus, the subject compounds are effective HIV protease inhibitors. It is contemplated that the subject compounds will also inhibit other retroviruses such as other lentiviruses in particular other strains of HIV, e.g. HIV-2, human T-cell leukemia virus, respiratory syncitial virus, simia immunodeficiency virus, feline leukemia virus, feline immuno-deficiency virus, hepadnavirus, cytomegalovirus and picornavirus. Thus, the subject compounds are effective in the treatment and/or proplylaxis of retroviral infections.

The subject compounds are also effective in preventing the growth of retroviruses in a solution. Both human and animal cell cultures, such as T-lymphocyte cultures, are utilized for a variety of well known purposes, such as research and diagnostic procedures including calibrators and controls. Prior to and during the growth and storage of a cell culture, the subject compounds may be added to the cell culture medium at an effective concentration to prevent the unexpected or undesired replication of a retrovirus that may inadvertently or unknowingly be present in the cell culture. The virus may be present originally in the cell culture, for example HIV is known to be present in human T-lymphocytes long before it is detectable in blood, or through exposure to the virus. This use of the subject compounds prevents the unknowing or inadvertent exposure of a potentially lethal retrovirus to a researcher or clinician.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula (I)

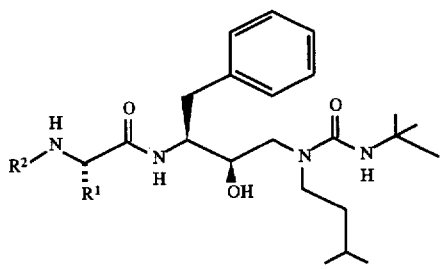

or a pharmaceutically acceptable salt or ester thereof, wherein $R^1$ is iso-propyl, sec-butyl, tert-butyl, —C(CH$_3$)$_2$(SCH$_3$), —C(CH$_3$)$_2$(S{O}CH$_3$) or —C(CH$_3$)$_2$(S{O$_2$}CH$_3$); and $R^2$ is N-methyl-L-alaninyl, N-methyl-D-alaninyl, glycinyl, N-methylglycinyl, L-prolyl, D-prolyl or L-isoleucinyl, each of which is optionally substituted on the nitrogen atom with benzyloxycarbonyl or tert-butoxycarbonyl.

2. The compound of claim 1 which is
(2R,3S)-3-(N-methylaminoacetyl-L-tert-butylglycinyl)amino-1-[N-isoamyl-N-(tert-butylcarbamoyl)]amino-4-phenyl-2-butanol;
(2R,3S)-3-(N-methylaminoacetyl-L-valinyl)amino-1-[N-isoamyl-N-(tert-butylcarbamoyl)]amino-4-phenyl-2-butanol;
(2R,3S)-3-(N-methylaminoacetyl-L-isoleucinyl)amino-1-[N-isoamyl-N-(tert-butylcarbamoyl)]amino-4-phenyl-2-butanol;
(2R,3S)-3-(N-methylaminoacetyl-S-methyl-L-penicillaminyl) amino-1-[N-isoamyl-N-(tert-butylcarbamoyl)]amino-4-phenyl-2-butanol;
(2R,3S)-3-(N-methyl-L-alaninyl-L-tert-butylglycinyl)amino-1-[N-isoamyl-N-(tert-butylcarbamoyl)]amino-4-phenyl-2-butanol;
(2R,3S)-3-(N-methyl-D-alaninyl-L-tert-butylglycinyl)amino-1-[N-isoamyl-N-(tert-butylcarbamoyl)]amino-4-phenyl-2-butanol;
(2R,3S)-3-(glycinyl-L-tert-butylglycinyl)amino-1-[N-isoamyl-N-(tert-butylcarbamoyl)]amino-4-phenyl-2-butanol;
(2R,3S)-3-(L-prolyl-L-tert-butylglycinyl)amino-1-[N-isoamyl-N-(tert-butylcarbamoyl)]amino-4-phenyl-2-butanol;
(2R,3S)-3-(D-prolyl-L-tert-butylglycinyl)amino-1-[N-isoamyl-N-(tert-butylcarbamoyl)]amino-4-phenyl-2-butanol;
(2R,3S)-3-(N-methyl-D-alaninyl-L-isoleucinyl)amino-1-[N-isoamyl-N-(tert-butylcarbamoyl)]amino-4-phenyl-2-butanol; or
(2R,3S)-3-(L-prolyl-L-isoleucinyl)amino-1-[N-isoamyl-N-(tert-butylcarbamoyl)]amino-4-phenyl-2-butanol.

3. The compound of claim 2 which is the hydrochloride salt or mesylate salt of the compound.

4. The compound of claim 2 which is (2R,3S)-3-(N-methylaminoacetyl-L-tert-butylglycinyl)amino-1-[N-isoamyl-N-(tert-butylcarbamoyl)]amino-4-phenyl-2-butanol or its hydrochloride salt.

5. The compound of claim 1 which is
(2R,3S)-3-(N-benzyloxycarbonyl-N-methyl-L-alaninyl-L-tert-butylglycinyl)amino-1-[N-isoamyl-N-(tert-butylcarbamoyl)]amino-4-phenyl-2-butanol;
(2R,3S)-3-(N-benzyloxycarbonyl-N-methyl-D-alaninyl-L-tert-butylglycinyl)amino-1-[N-isoamyl-N-(tert-butylcarbamoyl)]amino-4-phenyl-2-butanol;
(2R,3S)-3-(N-tert-butoxycarbonyl-glycinyl-L-tert-butylglycinyl)amino-1-[N-isoamyl-N-(tert-butylcarbamoyl)]amino-4-phenyl-2-butanol;
(2R,3S)-3-(N-benzyloxycarbonyl-L-prolyl-L-tert-butylglycinyl)amino-1-[N-isoamyl-N-(tert-butylcarbamoyl)]amino-4-phenyl-2-butanol;
(2R,3S)-3-(N-tert-butoxycarbonyl-L-prolyl-L-tert-butylglycinyl)amino-1-[N-isoamyl-N-(tert-butylcarbamoyl)]amino-4-phenyl-2-butanol;
(2R,3S)-3-(N-benzyloxycarbonyl-N-methyl-D-alaninyl-L-isoleucinyl)amino-1-[N-isoamyl-N-(tert-butylcarbamoyl)]amino-4-phenyl-2-butanol;
(2R,3S)-3-(N-benzyloxycarbonyl-L-prolyl-L-isoleucinyl)amino-1-[N-isoamyl-N-(tert-butylcarbamoyl)]amino-4-phenyl-2-butanol; or
(2R,3S)-3-(N-benzyloxycarbonyl-L-isoleucinyl-L-isoleucinyl)amino-1-[N-isoamyl-N-(tert-butylcarbamoyl)]amino-4-phenyl-2-butanol.

6. A compound selected from the group consisting of
(2R,3S)-3-(N,N-dimethylaminoacetyl-L-isoleucinyl)amino-1-[N-isoamyl-N-(tert-butylcarbamoyl)]amino-4-phenyl-2-butanol and
(2R,3S)-3-(N,N-dimethylaminoacetyl-S-methyl-L-penicillaminyl)amino-1-[N-isoamyl-N-tert-butylcarbamoyl)]amino-4-phenyl-2-butanol.

7. A pharmaceutical composition comprising a compound of claim 1 and a pharmaceutically acceptable carrier.

8. A pharmaceutical composition comprising a compound of claim 4 and a pharmaceutically acceptable carrier.

9. A method of inhibiting a retroviral protease comprising administering an effective amount of the composition of claim 7.

10. A method of inhibiting a retroviral protease in a mammal infected with a retrovirus comprising administering to said mammal an effective amount of the composition of claim 8.

11. The method of claim 10 wherein the retroviral protease is human immunodeficiency virus protease.

12. A composition comprising a mixture of (2R,3S)-3-(N-methylaminoacetyl-L-tert-butylglycinyl)amino-1-[N-isoamyl-N-(tert-butylcarbamoyl)]amino-4-phenyl-2-butanol or its hydrochloride salt and (2R,3S)-3-(N,N-dimethylaminoacetyl-L-tert-butylglycinyl)amino-1-[N-isoamyl-N-(tert-butylcarbamoyl)]amino-4-phenyl-2-butanol or its hydrochloride salt.

13. A composition comprising a mixture of (2R,3S)-3-(N-methylaminoacetyl-L-isoleucinyl)amino-1-[N-isoamyl-N-(tert-butylcarbamoyl)]amino-4-phenyl-2-butanol or its hydrochloride salt and (2R,3S)-3-(N,N-dimethylaminoacetyl-L-isoleucinyl)amino-1-[N-isoamyl-N-(tert-butylcarbamoyl)]amino-4-phenyl-2-butanol or its hydrochloride salt.

14. A method of treating a retroviral infection in a mammal suffering therefrom comprising administering to said mammal an effective amount of a compound of the formula

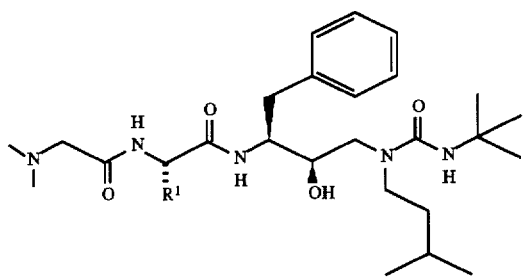

or a pharmaceutically acceptable salt thereof, and an effective amount of a compound of formula

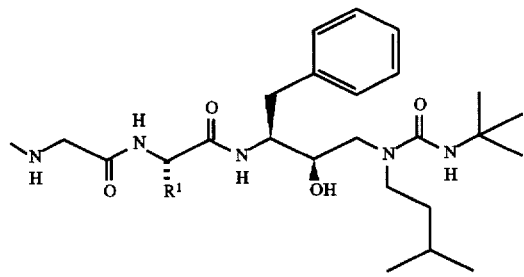

or a pharmaceutically acceptable salt thereof, wherein $R^1$ is iso-propyl, sec-butyl, tert-butyl, —C(CH$_3$)$_2$(SCH$_3$), —C(CH$_3$)$_2$(S{O}CH$_3$) or —C(CH$_3$)$_2$(S{O}$_2$CH$_3$).

15. The method of claim 14 wherein the mammal is a human and the retrovirus is immunodeficiency virus.

16. A method of treating a retroviral infection in a mammal suffering therefrom comprising administering to said mammal an effective amount of a compound of claim 1 and at least one antiviral agent which is a nucleoside analog, a nonnucleoside reverse transcriptase inhibitor, a tat antagonist or a glycosidase inhibitor.

17. The method of claim 16 wherein said nucleoside analog is AZT, DDI, DDC, 3TC, DAT or PMEA and said glycosidase inhibitor is castanospermine or N-butyl-1-deoxynojirimycin.

* * * * *